United States Patent
Burbank et al.

(10) Patent No.: US 8,152,737 B2
(45) Date of Patent: *Apr. 10, 2012

(54) TISSUE SPECIMEN ENCAPSULATION DEVICE AND METHOD THEREOF

(75) Inventors: Fred H. Burbank, San Juan Capistrano, CA (US); Richard L. Quick, Trabuco Canyon, CA (US); Jacob Frank Louw, Carlsbad, CA (US); Michael L. Jones, Capistrano Beach, CA (US); Paul Lubock, Laguna Niguel, CA (US)

(73) Assignee: Senorx, Inc., Irvine, CA (US)

( * ) Notice: Subject to any disclaimer, the term of this patent is extended or adjusted under 35 U.S.C. 154(b) by 687 days.

This patent is subject to a terminal disclaimer.

(21) Appl. No.: 11/811,952

(22) Filed: Jun. 12, 2007

(65) Prior Publication Data

US 2008/0077045 A1 Mar. 27, 2008

Related U.S. Application Data

(63) Continuation of application No. 10/342,867, filed on Jan. 14, 2003, now Pat. No. 7,229,418, which is a continuation of application No. 10/032,083, filed on Dec. 21, 2001, now Pat. No. 6,508,773, which is a continuation of application No. 09/208,535, filed on Dec. 9, 1998, now Pat. No. 6,344,026, which is a continuation-in-part of application No. 09/057,303, filed on Apr. 8, 1998, now Pat. No. 6,331,166.

(60) Provisional application No. 60/076,973, filed on Mar. 3, 1998.

(51) Int. Cl.
*A61B 10/00* (2006.01)
*A61B 18/18* (2006.01)
*A61B 17/32* (2006.01)

(52) U.S. Cl. .................. 600/564; 600/567; 606/167

(58) Field of Classification Search .................. 600/564, 600/565, 566, 567, 568; 606/39, 45, 167, 606/170

See application file for complete search history.

(56) References Cited

U.S. PATENT DOCUMENTS 2,032,860 A 3/1936 Wappler et al.
(Continued)

FOREIGN PATENT DOCUMENTS

DE 19528440 A1 8/1995
(Continued)

OTHER PUBLICATIONS

Armstrong, J.S. et al., "Differential marking of excision planes in screened breast lesions by organically coloured gelantins [see comments].", *Journal of Clinical* Pathology, (Jul. 1990), 43(7) 604-7, XP000971447 abstract; tables 1 and 2.

(Continued)

*Primary Examiner* — Max Hindenburg
*Assistant Examiner* — Jonathan M Foreman

(57) ABSTRACT

A device for encapsulating tissue specimens includes a wand assembly, a sheath, and a guide assembly. The guide assembly pulls, draws, or otherwise moves the sheath about the tissue specimen. The wand assembly is disposed proximate to the tissue specimen, typically either adjacent or through the specimen. In an aspect of the encapsulating device, the guide assembly has sheath deployment members that are disposed about the tissue specimen. The sheath, which is attached to ends of the sheath deployment members and the wand assembly, is drawn over the tissue specimen as the sheath deployment members are pushed or pulled. The guide assembly is an arm or a housing that rotates about the tissue specimen. The sheath, which is secured at one end to the guide assembly and at another end to the wand assembly, is drawn over the tissue specimen as the guide assembly rotates.

9 Claims, 18 Drawing Sheets

U.S. PATENT DOCUMENTS

| | | |
|---|---|---|
| 3,805,791 A | 4/1974 | Seuberth et al. |
| 3,844,272 A | 10/1974 | Banko |
| 3,955,578 A | 5/1976 | Chamness et al. |
| 4,202,338 A | 5/1980 | Bitroff |
| 4,294,254 A | 10/1981 | Chamness |
| 4,311,143 A | 1/1982 | Komiya |
| 4,362,160 A | 12/1982 | Hiltebrandt |
| 4,503,855 A | 3/1985 | Maslanka |
| 4,576,162 A | 3/1986 | McCorkle |
| 4,611,594 A * | 9/1986 | Grayhack et al. ............ 606/127 |
| 4,638,802 A | 1/1987 | Okada |
| 4,718,419 A | 1/1988 | Okada |
| 4,724,836 A | 2/1988 | Okada |
| 5,007,908 A | 4/1991 | Rydell |
| 5,024,617 A | 6/1991 | Karpiel |
| 5,035,696 A | 7/1991 | Rydell |
| 5,037,379 A | 8/1991 | Clayman et al. |
| 5,064,424 A | 11/1991 | Bitrolf |
| 5,066,295 A | 11/1991 | Kozak et al. |
| 5,078,716 A | 1/1992 | Doll |
| 5,080,660 A | 1/1992 | Buelna |
| 5,085,659 A | 2/1992 | Rydell |
| 5,100,423 A | 3/1992 | Fearnot |
| 5,147,307 A | 9/1992 | Gluck |
| 5,158,561 A | 10/1992 | Rydell et al. |
| 5,163,938 A | 11/1992 | Kambara et al. |
| 5,192,270 A | 3/1993 | Carswell, Jr. |
| 5,196,007 A | 3/1993 | Ellman et al. |
| 5,201,732 A | 4/1993 | Parins et al. |
| 5,201,741 A | 4/1993 | Dulebohn |
| 5,207,686 A | 5/1993 | Dolgin |
| 5,215,521 A | 6/1993 | Cochran et al. |
| 5,217,458 A * | 6/1993 | Parins ............................. 606/48 |
| 5,224,488 A | 7/1993 | Neuffer |
| 5,304,176 A | 4/1994 | Phillips |
| 5,312,400 A | 5/1994 | Bales et al. |
| 5,318,564 A | 6/1994 | Eggers |
| 5,323,768 A | 6/1994 | Saito et al. |
| 5,324,288 A | 6/1994 | Billings et al. |
| 5,335,671 A | 8/1994 | Clement |
| 5,337,754 A | 8/1994 | Heaven et al. |
| 5,344,420 A | 9/1994 | Hilal et al. |
| 5,374,188 A | 12/1994 | Frank et al. |
| 5,376,094 A | 12/1994 | Kline |
| 5,380,321 A | 1/1995 | Yoon |
| 5,395,312 A | 3/1995 | Desai |
| 5,403,310 A | 4/1995 | Fisher |
| 5,415,656 A | 5/1995 | Tihon et al. |
| 5,417,687 A | 5/1995 | Nardella et al. |
| 5,417,697 A | 5/1995 | Wilk et al. |
| 5,423,809 A | 6/1995 | Klicek |
| 5,437,665 A | 8/1995 | Munro |
| 5,441,503 A | 8/1995 | Considine et al. |
| 5,462,553 A | 10/1995 | Dolgin |
| 5,484,436 A | 1/1996 | Eggers et al. |
| 5,501,654 A | 3/1996 | Failla et al. |
| 5,526,822 A | 6/1996 | Burbank et al. |
| 5,542,948 A | 8/1996 | Weaver et al. |
| 5,554,159 A | 9/1996 | Fischer |
| 5,611,803 A | 3/1997 | Heaven et al. |
| 5,643,282 A | 7/1997 | Kieturakis |
| 5,649,547 A | 7/1997 | Ritchart et al. |
| 5,665,085 A | 9/1997 | Nardella |
| 5,674,184 A | 10/1997 | Hassler, Jr. |
| 5,730,726 A | 3/1998 | Klingenstein et al. |
| 5,769,086 A | 6/1998 | Richart et al. |
| 5,769,794 A | 6/1998 | Conlan et al. |
| 5,782,775 A | 7/1998 | Milliman et al. |
| 5,788,709 A | 8/1998 | Riek et al. |
| 5,794,626 A | 8/1998 | Kieturakis |
| 5,795,308 A | 8/1998 | Russin |
| 5,810,806 A | 9/1998 | Ritchart et al. |
| 5,848,978 A | 12/1998 | Cecchi |
| 5,857,981 A | 1/1999 | Bucalo et al. |
| 5,857,982 A | 1/1999 | Milliman et al. |
| 5,913,857 A | 6/1999 | Ritchart et al. |
| 5,925,044 A | 7/1999 | Hoffmann et al. |
| 6,344,026 B1 * | 2/2002 | Burbank et al. ............ 600/567 |
| 6,454,727 B1 | 9/2002 | Burbank et al. |
| 6,494,881 B1 | 12/2002 | Bales et al. |
| 6,508,773 B2 * | 1/2003 | Burbank et al. ............ 600/567 |
| 6,712,775 B2 | 3/2004 | Burbank et al. |

FOREIGN PATENT DOCUMENTS

| | | |
|---|---|---|
| EP | 0 472 368 A2 | 8/1991 |
| GB | 2311468 A | 2/1997 |
| WO | WO 93/07811 A | 4/1983 |
| WO | WO 95/02370 | 1/1995 |
| WO | WO 95/02371 | 1/1995 |
| WO | WO 97/13460 | 4/1997 |
| WO | WO 97/35522 A | 10/1997 |
| WO | WO 98/06346 | 2/1998 |
| WO | WO 98/08441 | 3/1998 |
| WO | WO 99 04704 A | 2/1999 |

OTHER PUBLICATIONS

Lorentzen, T. et al., "The Loop Electrode: a New Device for US-guided Interstitial Tissue Ablation Using Radio frequency Electrosurgery-An Animal Study", 1996 Blackwell Science Ltd., *Min Invas Ther & Allied Technol*, 1996, pp. 5, 511-516.

* cited by examiner

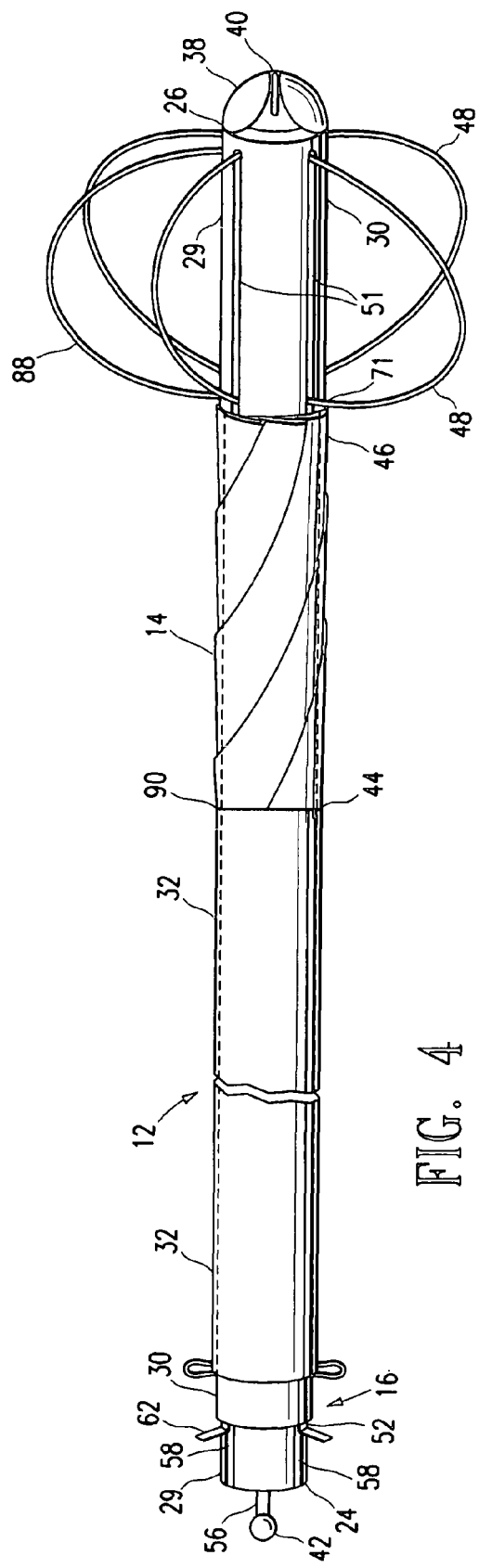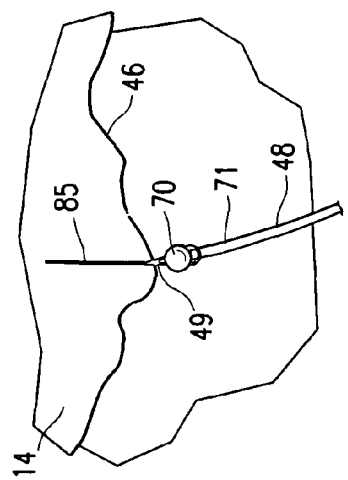
FIG. 4
FIG. 4A

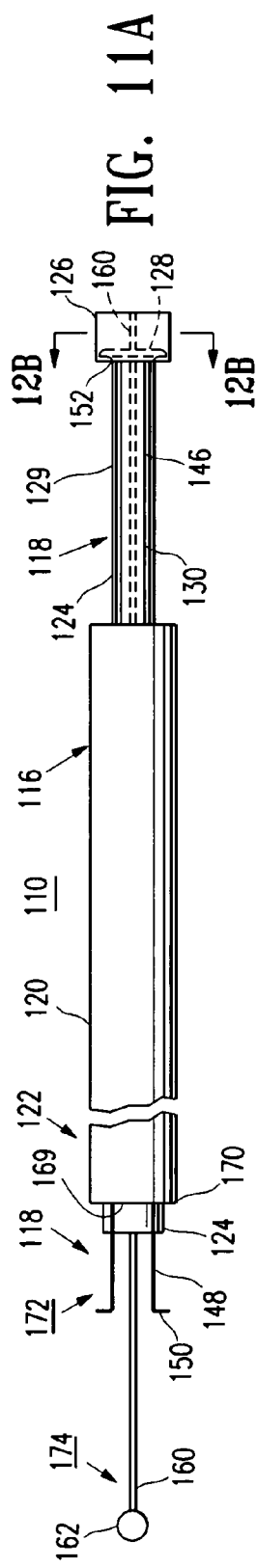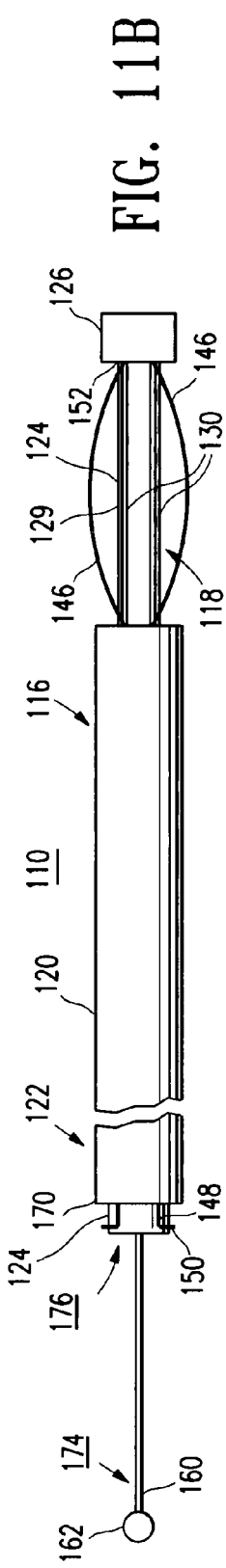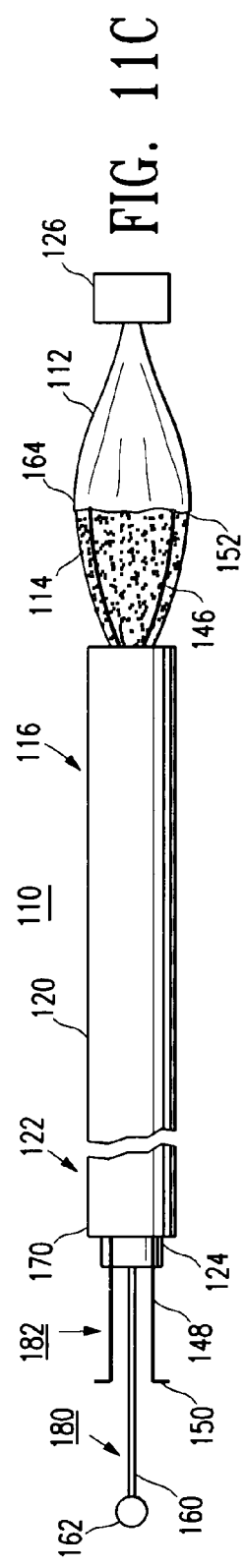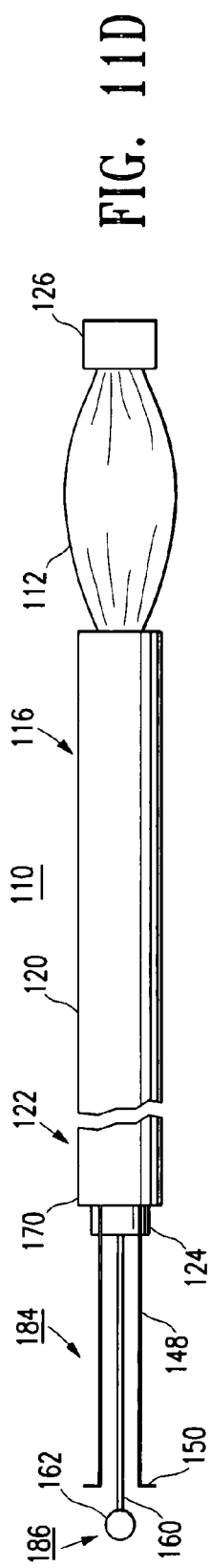

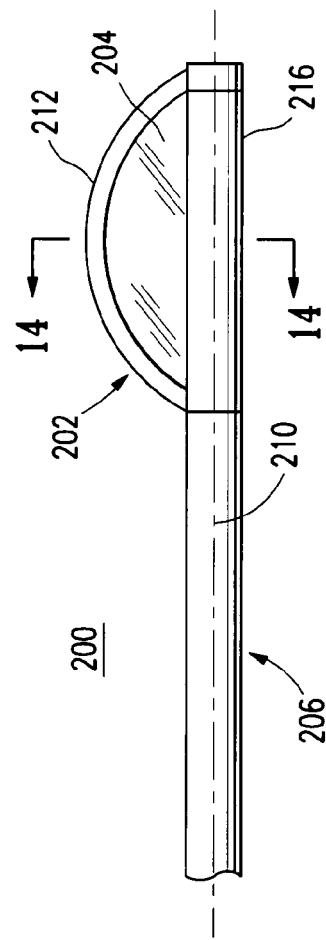
FIG. 13
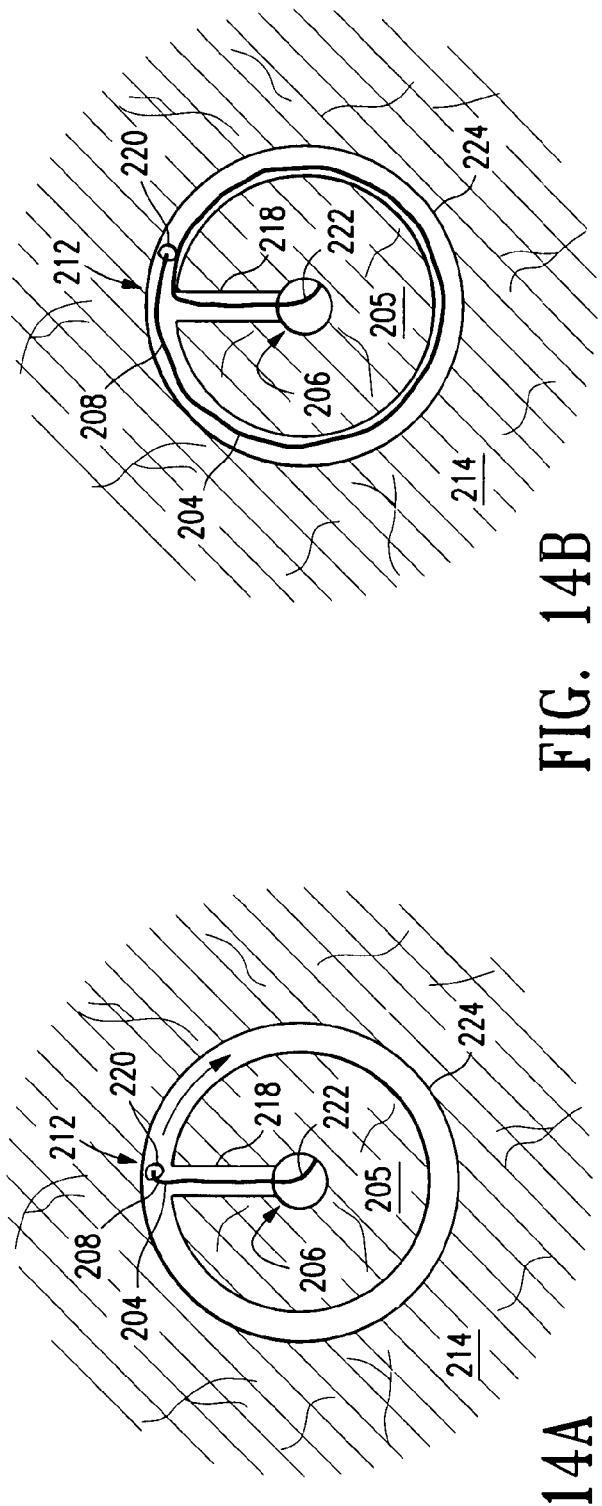
FIG. 14B
FIG. 14A

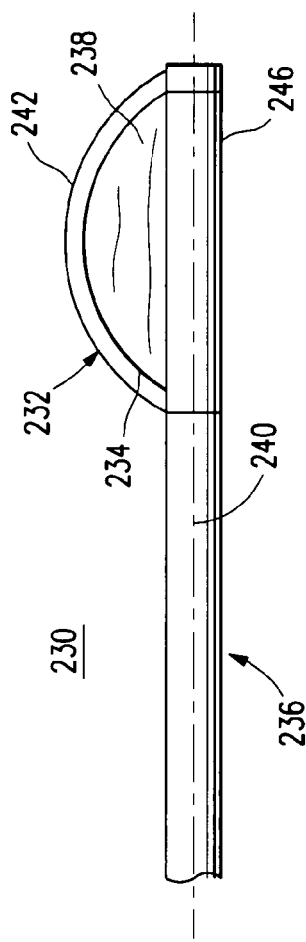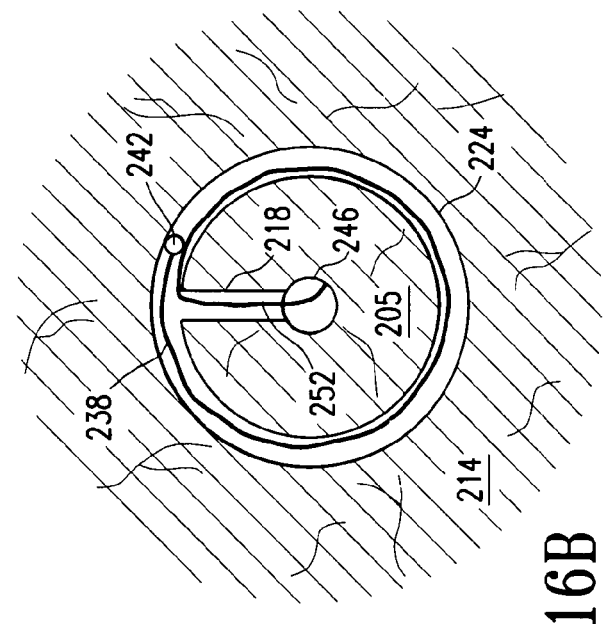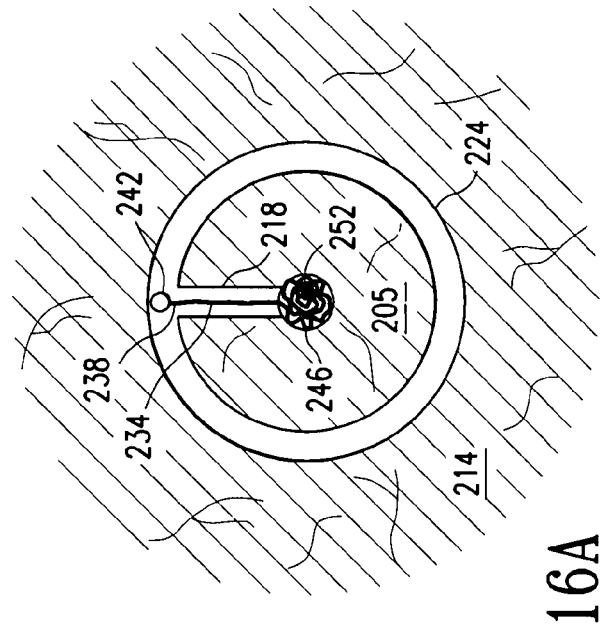

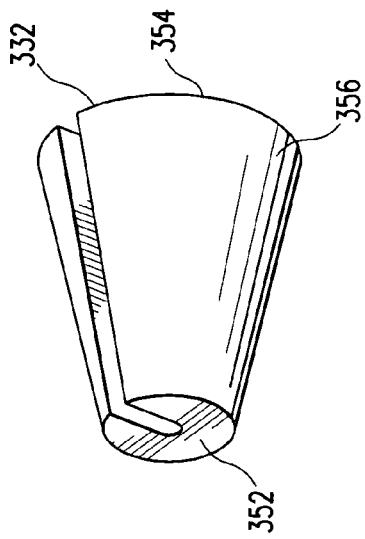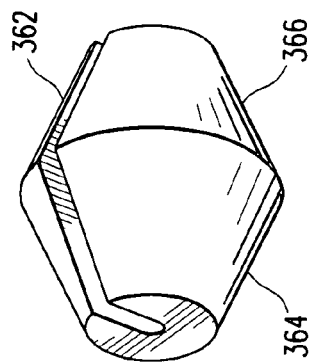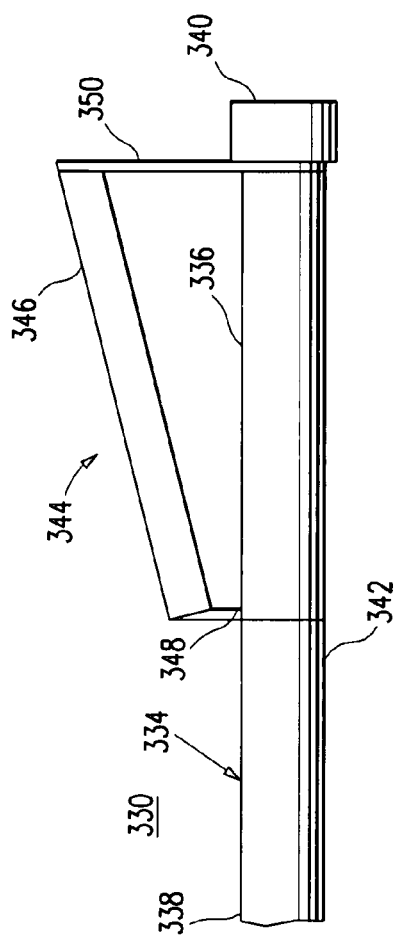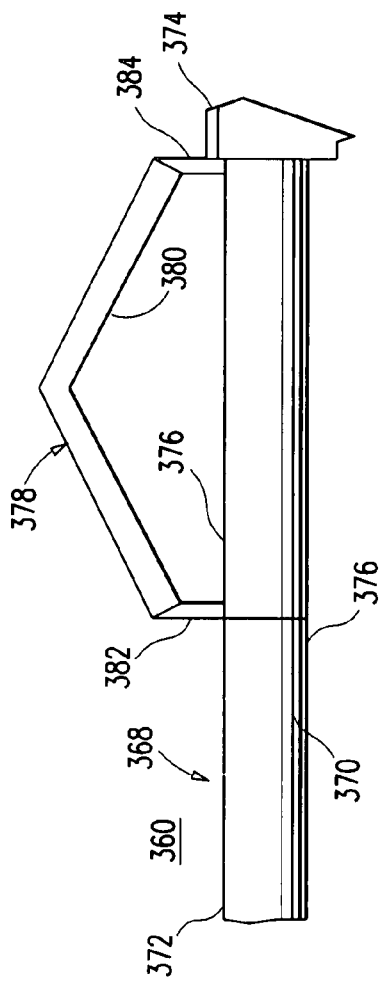

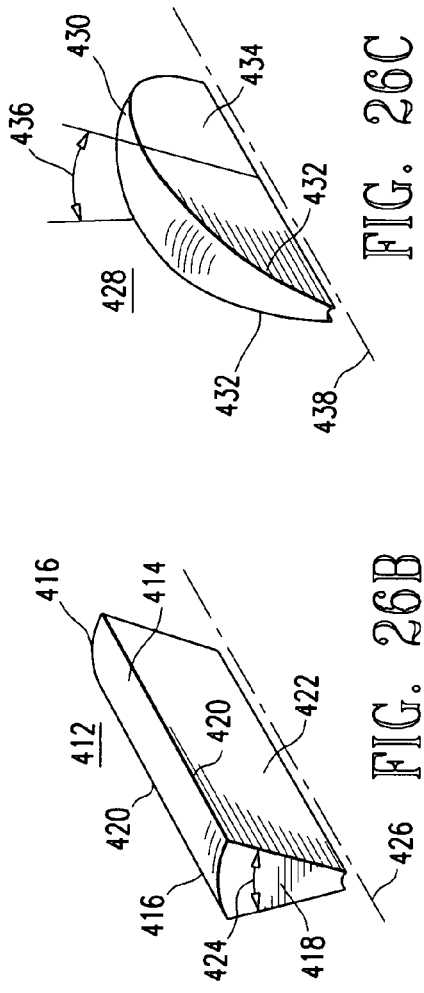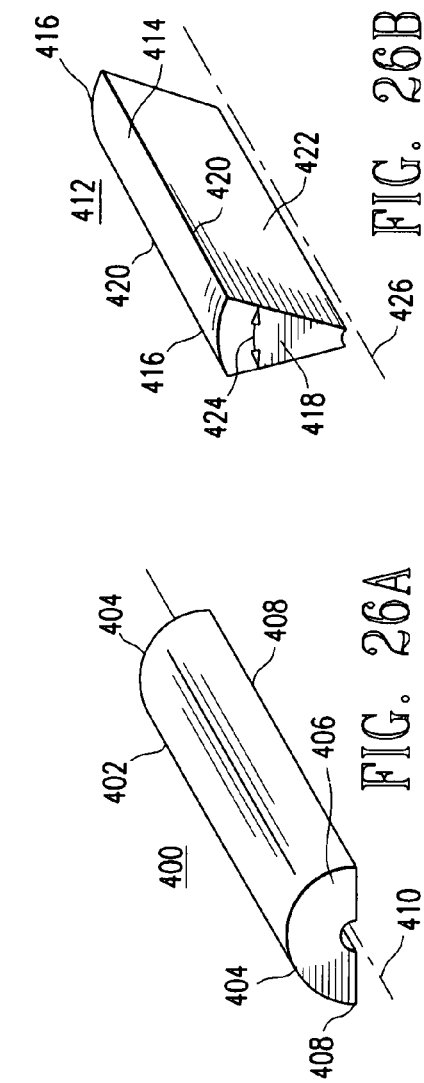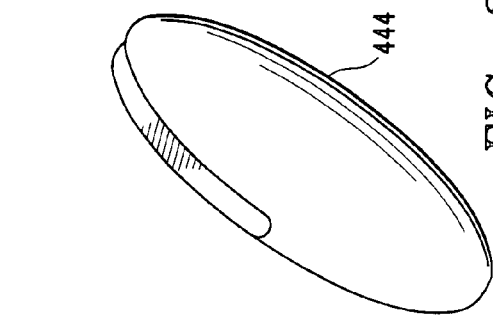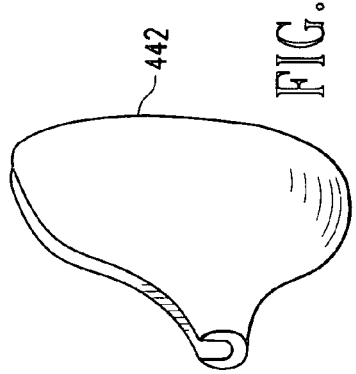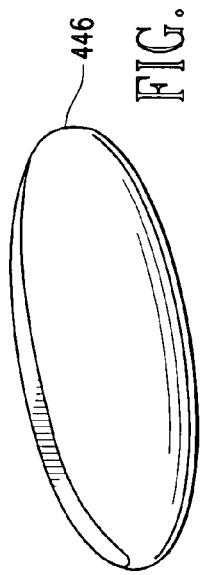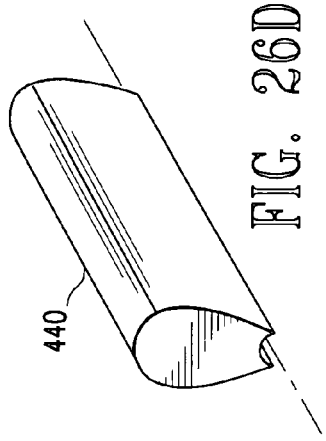

TISSUE SPECIMEN ENCAPSULATION DEVICE AND METHOD THEREOF

RELATED APPLICATIONS

This application is a continuation of application Ser. No. 10/342,867 filed Jan. 14, 2003, now U.S. Pat. No. 7,229,418, which is a continuation of application Ser. No. 10/032,083, filed on Dec. 21, 2001, now U.S. Pat. No. 6,508,773, which is a continuation of application Ser. No. 09/208,535, filed on Dec. 9, 1998, now U.S. Pat. No. 6,344,026, which is a continuation-in-part of U.S. patent application Ser. No. 09/057,303, filed Apr. 8, 1998, now U.S. Pat. No. 6,331,166, and entitled BREAST BIOPSY SYSTEM AND METHOD, which claims priority benefit of provisional application Ser. No. 60/076,973, filed Mar. 3, 1998. Each of the nonprovisional applications are incorporated herein by reference in their entireties. Priority is claimed to all the applications.

BACKGROUND OF THE INVENTION

This invention relates to biopsy devices and, more specifically, to devices that encapsulate a tissue specimen.

The prior art discloses numerous methods for surgically removing an internal tissue specimen from a target body. Techniques and the requisite medical devices exist to remove tissue specimens of all sizes. A basic technique is to make an incision proximate to the area of the tissue specimen and excise it with a scalpel. This technique can be extremely invasive, result in trauma to proximate tissue and a maximum amount of scar tissue, and leads to additional healthy tissue being removed unnecessarily.

The prior art also discloses techniques and methods that are less invasive than excising the tissue sample with a scalpel. As disclosed in U.S. Pat. No. 5,788,709, a trocar is inserted into the target body, the target body is insufflated and the tissue specimen is severed. The tissue specimen may be a cyst, a tumor, parts of an organ, a whole organ, a diseased portion of the body, a biopsy sample, or any other specimen that is desired to be removed.

The prior art further discloses many techniques for removing the tissue specimen. Proper removal of the tissue specimen is critical. Cysts and other types of diseased tissue may spill into the surrounding tissue, resulting in inflammation and transfer of malignant cells or disease. Tumors or organs larger than the trocar need to be segmented for removal, which also may lead to inflammation and transfer of malignant cells. The segmenting of the tumors or organs is technically complicated and very time consuming. In certain methods, such as motor driven morcellators, there is a high danger of injury for the organs and blood vessels in the body. Further, morcellators render the tissue specimen unusable for certain pathologies.

Devices and techniques for removing the tissue specimen while limiting the transfer of malignant or diseased cells are also disclosed in the prior art. U.S. Pat. No. 5,037,379 discloses a surgical tissue bag for percutaneously debulking tissue. The debulking is performed by inserting the bag through an access sheath into a body cavity, inserting a surgically removed tissue mass through an open end of the bag, closing the end of the bag and pulling the closed end of the bag out of the body cavity. The end of the bag is then opened and morcellating or debulking of the tissue through the open end of the bag is performed while the remainder of the bag remains in the body cavity. The bag is made of flexible and foldable material and includes an inner layer of puncture resistant material such as nylon in either woven or solid layer form for resisting penetration by a surgical morcellating instrument. The outer layer of the bag is made of a moisture proof polymeric material.

U.S. Pat. No. 5,215,521 discloses an entrapment envelope having a means for opening and closing. The entrapment envelope is constructed of flexible, low fluid permeability materials having sufficient strength to contain morcellator entry, organ fragmentation and removal.

U.S. Pat. No. 5,337,754 discloses a tissue isolation bag which expands from a collapsed configuration to an expanded configuration when pressurized gas or liquid is supplied thereto.

U.S. Pat. No. 5,330,483 discloses a tissue reduction device which is thermally activated and is used in conjunction with a tissue isolation bag. The tissue reduction member is in an expanded condition at body temperature but shrinks to a smaller specimen reduced configuration when heated to a temperature above body temperature.

U.S. Pat. No. 5,611,803 discloses a tissue segmentation device incorporated into an isolation bag for segmenting tissue during an operation such as in laparoscopic surgery. The device includes one or more loops of high strength wire which can be mechanically reduced in loop diameter to cut tissue into smaller pieces. The wire loops can be heated electrically to aid in the cutting through hard-to-cut parts of the tissue. The wire can be of a shape memory alloy which shrinks when heated to form a smaller diameter loop.

U.S. Pat. No. 5,788,709 discloses a tissue specimen being removed with a bag having a side opening and an end opening. The bag is inserted into the abdominal cavity with the end opening of the bag remaining extracorporeal to a thread casing that extends through the abdominal wall. The tissue specimen is directed through the side opening and into the bag. The bag is reduced in size to snugly hold the tissue specimen. The tissue specimen is then segmented. The bag has positioning pins to hold the tissue specimen in place in the bag during the segmenting process. The segmented tissue specimen is removed through the end opening.

The bags disclosed in the prior art for retaining the tissue specimen and performing various procedures on the specimen have the disadvantage of requiring a relatively large sized insufflated region to perform the encapsulation.

U.S. Pat. No. 5,417,697 discloses a polyp removal device that severs and removes the polyp. The snare is an electrically conductive cauterization loop that is ejected from the end of an endoscopic assembly. A cup-shaped web member is also ejected from the endoscopic assembly end. The loop is placed over the polyp and the web member is opened up. A vacuum is applied to the web member to secure the polyp in the cup-shaped web member. Electrical current is conducted to the loop to sever the polyp from the patient, and the loop is closed. The severed polyp is held in the web member by suction and is removed from the patient. This device has the restriction of being used with polyps. Additionally, the entire polyp is not enclosed, resulting in possible contamination of tissue during the removal procedure.

U.S. Pat. No. 5,643,282 discloses a surgical instrument to remove excised tissue from an insufflated anatomic cavity through a body wall overlaying an endoscopic work space. A tissue grasping instrument attaches itself to the excised tissue and the tissue is pulled through a sleeve, or snake, which extends through the body wall. This device has numerous disadvantages, including the restriction of grasping the tissue specimen, which may (resulting) in severing portions of the tissue specimen which in turn remain in the patient to cause inflammation, spreading of disease, and contamination by malignant cells.

Further, the cited prior art does not disclose devices or techniques suitable for removing a cyst or a tumor from a region that is not insufflated while minimizing deposition of cells therefrom into the patient, such as removing a tumor from a breast.

SUMMARY OF THE INVENTION

Objects of the invention are met by a device for encapsulating a tissue specimen prior to withdrawal from a body. The device comprises a wand assembly, a sheath, and a guide assembly. The wand assembly defines an axis, and axial direction, and a radial direction. The sheath comprises a first portion that is connected to the wand assembly and a second portion. The guide assembly is connected to the sheath second portion, wherein the guide assembly is capable of positioning the sheath about at least a portion of the tissue specimen. In an aspect of the invention, the sheath is made of one piece. In another aspect of the invention, the sheath is made up of a plurality of noncontiguous segments. In a further aspect of the invention, adjacent noncontiguous segments overlap when the sheath is positioned about at least a portion of the tissue specimen.

The tissue specimen may take many shapes. In one aspect of the invention, the tissue specimen is of a generally rotational form. In further aspects of the invention, the tissue specimen is generally spherical, generally cylindrical, or generally ellipsoidal. Further, the tissue specimen may comprise a plurality of surfaces. The tissue specimen may also comprise a surface of a partial rotation. In a further aspect of the invention, the tissue specimen may be a segment of a generally rotational form. In another aspect of the invention, the tissue specimen is of a generally eccentric rotational form.

In an aspect of the invention, the guide assembly is capable of moving the sheath second portion in the axial direction. In other aspects of the invention the guide assembly is capable of moving the sheath second portion in a direction that is not the axial direction.

In an aspect of the invention where the guide assembly is capable of moving the sheath second portion in the axial direction, the sheath first portion is attached to the wand assembly. Further, the sheath extends from the first portion and terminates at the second portion. The sheath second portion defines an opening in the sheath through which the wand assembly extends. The opening has a diameter that is at least a maximum cross second of the tissue specimen in a plane that is generally normal to the wand assembly axis. In a further aspect of the invention, the tissue sample is positioned adjacent to the wand assembly and the sheath is positioned about at least a portion of the tissue specimen. In another aspect of the invention, the tissue sample is positioned about the wand assembly and the sheath is positioned about at least a portion of the tissue specimen.

In an aspect of the invention, the guide assembly comprises at least a sheath deployment member having an attachment end and a deployment end. The attachment end is attached to the sheath second portion with the sheath deployment member being arranged such that moving the sheath deployment member deployment end in the wand assembly axial direction results in the sheath deployment member guiding the second portion over the tissue specimen. Aspects of the invention may incorporate any suitable sheath deployment member including twine; cordage; filament; wire; a line; a band; a strap; a strand; and woven, braided, twisted, knit, looped, linked, metal, plastic, composite materials.

In an aspect of the invention, the wand assembly comprises a shaft having a distal end, a proximal end, a mid-section therebetween, an outside surface, and an axial hollow center. The shaft distal section comprises an orifice extending through the shaft to the hollow center. The first portion of the sheath is attached to the shaft mid-portion while the sheath second portion is proximate to the mid-portion. The sheath deployment member extends through the orifice and into the shaft hollow center. The sheath deployment member has a first portion that extends in the wand assembly axial direction from the attachment end to the shaft orifice. The sheath deployment member has a second portion that extends from the orifice, into the shaft hollow center, and terminates at the sheath deployment member deployment end. Moving the sheath deployment member deployment end in the wand assembly axial direction and away from the shaft distal end results in the sheath deployment member drawing the sheath second portion opening from the shaft mid-portion and toward the shaft distal end. In an aspect of the invention, the sheath is positioned about at least a portion of the tissue specimen with the sheath second portion being proximate to the shaft distal end. In an aspect of the invention, the tissue sample is disposed proximally to the wand assembly between the sheath first portion and the shaft distal end. The tissue sample may be disposed about the wand assembly or disposed adjacent to the wand assembly.

In another aspect of the invention, the wand assembly comprises a shaft having a distal end, a proximal end, and an outside surface. Both the sheath first portion and second portion are proximate to the shaft distal end. The sheath deployment member is generally oriented in the wand assembly axial direction and proximate to the shaft outside surface with the deployment of the sheath deployment member extending toward the shaft proximal end. In an aspect of the invention, at least a portion of the sheath is positioned in a hollow core that is at the shaft distal end. After encapsulation, the sheath is positioned over the tissue sample with the sheath second portion located distal to the shaft distal end. Additionally, the sheath deployment member extends from the sheath second portion and away from the shaft distal end. The tissue sample is disposed proximate to the wand assembly and proximally to the shaft distal end. The tissue sample may be disposed either about the wand assembly or disposed adjacent to the wand assembly.

In an additional embodiment of the invention, the sheath unfurls about the specimen in a rotational manner. The guide assembly of the device is capable of moving rotationally the sheath second portion about the tissue specimen. The axis of rotation of the sheath second portion may be parallel to the wand assembly axis. In a further aspect of the invention, the sheath second portion axis of rotation is generally co-existent with the wand assembly axis.

In a further aspect of the invention, the guide assembly comprises a wrapper assembly having a housing in which is disposed the sheath second portion and a tissue covering portion of the sheath. The wrapper assembly is capable of moving about at least a portion of the tissue specimen while depositing the sheath tissue covering portion thereon. In aspects of the invention, the sheath tissue covering portion is disposed in the housing in a rolled manner or a folded manner.

In a further aspect of the invention, the wand assembly has a shaft having a distal end, a proximal end, and a mid-point therebetween. Additionally, the wrapper assembly comprises a first end attached to the shaft distal end, a second end attached to the shaft mid-portion, with the housing extending between the wrapper assembly ends. In an aspect of the invention, the housing comprises an arch shape portion. In an aspect of the invention, the wrapper assembly first and second ends radially extend from the shaft. In a further aspect of the invention, the wrapper assembly first and second ends perpendicularly extend from the shaft, and the housing is generally straight.

In a further aspect of the invention in which the sheath is furled by an arm that rotates about the specimen. The sheath first portion extends along the shaft and generally between the wrapper assembly first end and the wrapper assembly second end. The tissue sample may be disposed adjacent to the shaft and between the shaft mid-portion and the distal end or disposed about the shaft and between the shaft mid-portion and distal end.

In an aspect of the invention in which the sheath unfurls about the specimen in a rotational manner, the guide assembly comprises an arm that is attached to the sheath second portion, the arm being capable of moving about at least a portion of the tissue specimen.

In a further aspect of the invention, the wand assembly comprises a shaft having a distal end, a proximal end, a mid-portion, and an outside surface. The arm comprises a first end attached to the shaft distal end and a second end attached to the shaft mid-portion. The sheath first portion is between the arm first end and the arm second end. In aspects of the invention, the arm may be arch shaped or the arm may have two ends that radially extend from the shaft. In a still further aspect of the invention, the arm has two ends that radially extend from the shaft to a connecting portion extending generally straight between the two ends. In a still further aspect of the invention, the arm has two ends that perpendicularly extend from the shaft. In an aspect of the invention, the sheath first portion generally extends between the arm first end and the arm second end along the arm. Further, the shaft may be hollow and the sheath first portion's disposed in the shaft. The sheath may be stored in the shaft in a rolled arrangement or in a folded arrangement in aspects of the invention. Again, the tissue sample may be disposed proximally to the wand assembly, may be disposed about the wand assembly, or may be disposed adjacent the wand assembly.

Relative to any of the aspects of the invention, the sheath may be comprised of a number of different materials. The sheath may be comprised of porous material, non-porous material, or selectively permeable material. Aspects of the invention may have a sheath that is comprised of woven material, braided material, knit material, web material, mesh material, a film material, a flexible laminate material, or of an elastic material.

In an aspect of the invention, the guide assembly is capable of positioning the sheath about substantially all the tissue specimen.

In an aspect of the invention, an actuator device is functionally connected to the encapsulating device. The actuator device is arranged to manipulate at least one of the components of the encapsulating device, the encapsulating device components comprising the wand assembly, the sheath, and the guide assembly.

In an aspect of the invention, a tissue cutting device is attached to the wand assembly and arranged such that it enlarges a passage for the encapsulated tissue specimen to travel through to exit the body. In a further aspect of the invention, the tissue cutting device comprises a cutting member with a first end that is attached to a midportion of the wand assembly and a second end that is attached to a distal end of the wand assembly. The cutting member extends radially from the wand assembly. In another aspect of the invention, the tissue cutting device comprises a cutting member that extends radially from a midportion of the wand assembly. Aspects of the invention may have the tissue cutting device, and is some aspects the cutting member or cutting member, connected to a radio frequency generator.

In an aspect of the invention, the wand assembly is rigid. In another aspect of the invention, the wand assembly is flexible. In another aspect of the invention, the wand assembly is articulatable to enable the wand assembly to be steered.

Objectives of the invention may also be met by a method of sheathing a tissue specimen comprising the steps of disposing an encapsulation device near the tissue specimen. The encapsulation device comprises a wand assembly, a sheath, and a guide assembly. The wand assembly defines an axial direction and a radial direction. The sheath comprises a first portion being connected to the wand assembly and second portion. The guide assembly is attached to the sheath second portion, wherein the guide assembly is capable of positioning the sheath about at least a portion of the tissue specimen. In another step of the method of sheathing a tissue specimen, the sheath is positioned about the tissue specimen portion by manipulating the guide assembly.

In an aspect of the invention, the disposing step comprises the step of inserting a distal end at the wand assembly through the tissue specimen. In another aspect of the invention, the disposing step comprises the step of inserting a distal end of the wand assembly adjacent to the tissue specimen. In an aspect of the invention, the positioning step comprises the step of directing the second portion over the tissue specimen in the axial direction. In another aspect of the invention, the positioning step comprises a step of directing the second portion over the tissue specimen in a rotational manner. In a further aspect of the invention, an axis of the rotational direction is parallel to the axial direction. In an aspect of the invention, the positioning step comprises a step of directing the guide assembly to move from a linear axial direction adjacent the wand assembly, through a gap extending radially and axially to an outer surface of the tissue specimen, and over a portion of the tissue specimen outer surface. In an aspect of the invention, the positioning step comprises the step of positioning the sheath about the entire tissue specimen.

In an aspect of the invention, the tissue specimen is disposed in a body. In a further aspect, the positioning the sheath step further comprises the step of drawing the second portion of the sheath through a periphery margin about the tissue specimen. In aspects of the invention, the disposing step may comprise the step of inserting the wand assembly into either an insufflated or non-insufflated region of the body.

In a further aspect of the invention, the method further comprises the step of withdrawing the wand assembly in the tissue specimen from the body after the positioning step. In a still further aspect of the invention, the withdrawing step comprises the step of enlarging a passage in the body through which the encapsulation device extends to facilitate removal of the tissue specimen from the body. In a further aspect of the invention, the enlarging the passage step comprises surgically expanding the passage. In a further aspect of the invention, the surgically expanding the passage step comprises radially extending a cutting device from the wand assembly. In an aspect of the invention, the surgically expanding the passage step comprises radially extending a cutting device from the wand assembly. In an aspect of the invention, the surgically expanding passage step comprises energizing a member of the guide assembly with a radio frequency generator and expanding the passage with the radio frequency energized guide assembly member.

In an aspect of the invention, the disposing step comprises the step of steering the wand assembly to the tissue specimen, wherein the wand assembly is articulatable.

Objectives of the invention are also met by a device for retrieving a tissue specimen from a body. The retrieving device has an axis, a distal end and an encapsulation assembly. The distal end is adapted for entering the body. The encapsulation assembly at least partially covers the tissue specimen prior to retrieving the tissue specimen from the body. In an aspect of the invention, the encapsulation assembly comprises an axially disposed band that is actuatable in a radial direction.

In another aspect of the invention, the encapsulation assembly comprises a plurality of bands disposed along the device axis, the bands being actuatable in a radial direction. In a further aspect of the invention, the bands have a distal end and a proximal end. The band distal ends are attached to a distal end of the retrieving device. The band proximal ends are attached to a midportion of the retrieving device. The retrieving device distal end is rotatable about the axis compared to the retrieving device midportion in order that the bands may be twisted about the tissue specimen. In an aspect of the invention, a flexible sheet spans between at least two of the bands. In a further aspect of the invention, the flexible sheet is a web.

Other and further objects and advantages will appear hereinafter.

BRIEF DESCRIPTION OF THE DRAWINGS

FIG. 4 is a perspective view of the device of FIG. 1 shown without an outer sleeve and with sheath deployment members and a cutting member bowed radially outward;

FIG. 4a is a detail of a sheath deployment member in a ligature that is connected to the sheath of the device of FIG. 1;

FIGS. 11a-d are side views of a biopsy tissue specimen encapsulating device that proximally draws a sheath over a tissue specimen according to an embodiment of the invention, the device being shown at various stages of encapsulating the tissue specimen;

FIG. 13 is a side view of a biopsy tissue specimen encapsulating device that rotationally encapsulates a tissue specimen with a sheath wherein the sheath is unfurled from a rotating housing according to an embodiment of the invention;

FIGS. 14a-b are sectional views of the device of FIG. 13 at various stages of encapsulation of the tissue specimen;

FIG. 15 is a side view of a biopsy tissue specimen encapsulating device that rotationally encapsulates a tissue specimen with a sheath wherein a rotating arm pulls the sheath from the interior of the device according to an embodiment of the invention;

FIGS. 16a-b are sectional views of the device of FIG. 15 at various stages of encapsulation of the tissue specimen;

FIG. 22 is a biopsy tissue specimen encapsulating device for rotationally encapsulating a truncated cone shaped tissue specimen according to an embodiment of the invention;

FIG. 23 is a perspective view of the truncated cone shaped tissue specimen that is encapsulated by the device of FIG. 22;

FIG. 24 is a biopsy tissue specimen encapsulating device for rotationally encapsulating a multisurface tissue specimen according to an embodiment of the invention;

FIG. 25 is a perspective view of the multisurface tissue specimen that is encapsulated by the device of FIG. 24; and FIGS. 26a-g are views of a non-exclusive set of various tissue specimen shapes that embodiments of the invention encapsulate.

DESCRIPTION OF THE PREFERRED EMBODIMENTS

Figure 1:
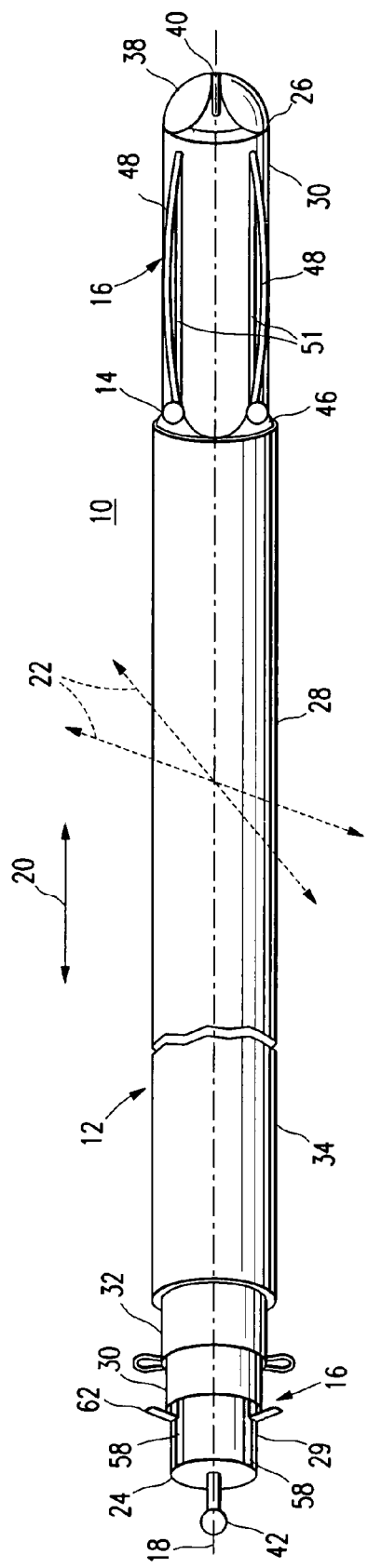
FIG. 1 is a perspective view of a biopsy tissue specimen encapsulating device that distally draws a sheath over a tissue specimen according to an embodiment of the invention.

Referring now to the figures, wherein like reference numerals refer to like elements throughout the figures, and referring specifically to FIGS. 1-4, a biopsy tissue specimen encapsulating device 10 according to the preferred embodiment of the invention is comprised of a wand assembly 12, a sheath 14, and a guide assembly 16.

The wand assembly 12 defines an axis 18, and axial direction 20, and a plurality of radial directions 22. The wand assembly 12 also has a proximal end 24, shown to the left in FIG. 1, and a distal end 26, shown to the right in FIG. 1. A midsection 28 extends between the ends 24 and 26. The proximal end 24 is the end that is held by a user of the device 10. Other embodiments of the invention may have the proximal end 24 functionally connected to an actuator system, such as a control box or the equivalent, that manipulates the device 10 per the directions of the user (not shown). Further details of the actuator system are discussed below.

The distal end 26 is inserted into a target body (not shown) and proximate to a tissue specimen to be encapsulated by the device. The body may be a patient of any species, live or deceased, or any other mass of matter that is distinct from other masses. The tissue specimen may be a cyst, a tumor, parts of an organ, a whole organ, a diseased portion of the body, a biopsy sample, or any other specimen that is desired to be removed from the target body. In embodiments of the invention, the wand assembly 12 may be rigid or flexible, and may be articulatable so that it may be steered. In embodiments with a flexible or articulatable wand assembly 12, the axis 18 is not linear, but rather curves with the wand assembly.

The wand assembly 12 comprises a shaft core 29, shaft 30, a sheath sleeve 32 and an outer sleeve 34. The shaft core 29, shaft 30 and sleeves 32 and 34 are co-axially aligned and nested such that the shaft core 29 is inside the shaft 30 that is inside the sheath sleeve 32 that is inside the outer sleeve 34. The shaft core 29 and the shaft 30 extend proximally and distally beyond the sleeves 32 and 34 with the shaft core extending proximally beyond the shaft. The sheath sleeve 32 extends proximally beyond the outer sleeve 34 but the outer sleeve 34 extends distally beyond the sheath sleeve 32.

In the shown embodiment, the distal end 26 of the device 10 has a tip 38 with a radio frequency ("RF") powered member 40 extending diametrically across the tip. The RF powered member 40 may be energized such that the device 10 moves through tissue via ablation or electrosurgical incision, thus enabling the device to be inserted into the target body containing a tissue specimen to be encapsulated. Other embodiments of the invention may have other means for the device to enter the biological target, such as lasers or other focussed light techniques, high pressure water, cutting with a sharp implement, cryogenic techniques, etc. Still other embodiments of the invention may not have a component analogous to the RF powered member 40 but the distal end 26 may be inserted into the target body through a pre-existing passage (not shown).

In the shown embodiment of the invention, a sheath deployment rod deployment end 42 extends from the proximal end 24 of the wand assembly 12. The sheath deployment member deployment end 42 is pulled proximally in the axial direction 20 to deploy the sheath 14 about a tissue specimen, as is described in more detail below.

Figure 2:
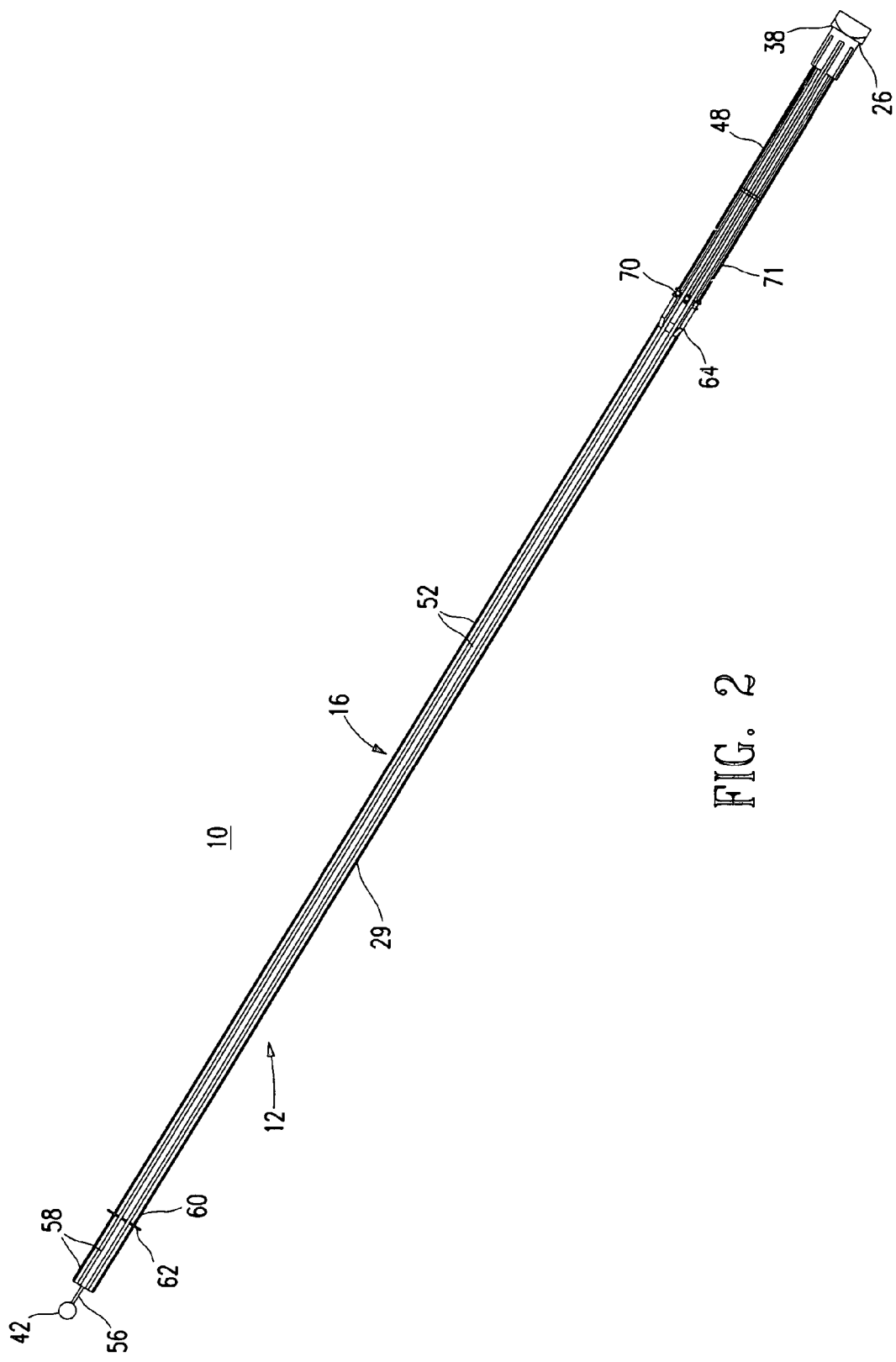
FIG. 2 is a perspective view of the device of FIG. 1 shown without an outer sleeve, a sheath sleeve, and a sheath.
Figure 3:
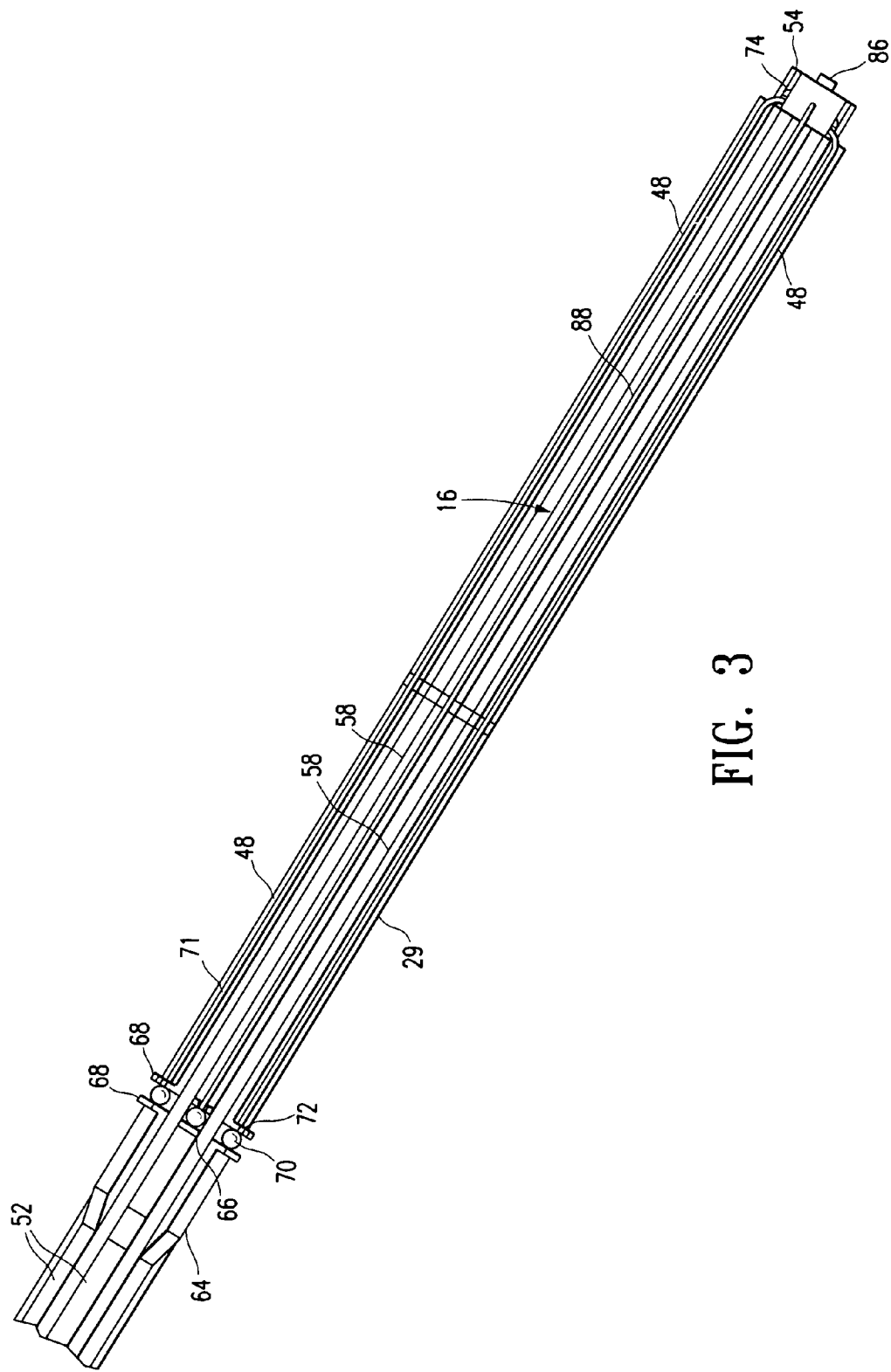
FIG. 3 is a perspective view of the details of the distal end of the device of FIG. 1 without an end cap, outer sleeve, and sheath.

Referring now more specifically to FIGS. 2 and 3, the device 10 is shown without the sheath sleeve 32, the outer sleeve 34, and the sheath 14 to better show the guide assembly 16. Further, the shaft 30 and the sheath 14 is removed to better show the guide assembly 16 and the shaft core 29. The guide assembly 16 is comprised of push rods 52, sheath deployment members 48, a sheath deployment member cap 54, and a sheath deployment member deployment rod 56 terminating in the sheath deployment rod deployment end 42. Other embodiments of the invention may have a member other than a rod, such as a member, functioning as the deployment rod 56.

The push rods 52 of the guide assembly 16 extend axially in grooves 58 in the shaft core 29. The shaft 30 fits over the shaft core 29 such that the push rods 52 may move axially and smoothly. The grooves 58, and therefore the push rods 52, are circumferentially spaced about the shaft. While the shown embodiment of the invention has five push rods 52, other embodiments of the invention may have more or less push rods. A proximal end 60 of the push rods 52 has a radially extending member 62 that is designed to enable the user of the device 10 to push or pull the rods. Other embodiments of the invention may have other arrangements to enable the user of the device, or the previously mentioned actuator system, to push or pull the rods 52.

At distal ends 64 of the push rods 52 are ball-holders 66. The ball-holders 66 are u-shaped with the legs 68 extending radially outward. Disposed in the ball-holders 66 are end-balls 70. The end balls 70 are located at the sheath deployment member attachment end 71. The sheath deployment members 48 extend from the end-balls 70 and through a radially extending slot 72 in the distally disposed leg 68 of the ball-holder 66. The sheath deployment members 48 continue distally to a sheath deployment member deployment end 74 in the sheath deployment member cap 54.

Referring back to FIG. 1, in the shown embodiment of the invention, the sheath deployment members 48 are slightly radially bowed and extend from slots 51 in the shaft 30. Other embodiments of the invention may have the sheath deployment members 48 not extending beyond the slots 51 or may have the sheath deployment members below the shaft 30. FIGS. 2 and 3 show the sheath deployment members 48 laying substantially straight and not bowed, as they may be disposed in an embodiment of the invention.

Embodiments of the invention may incorporate any suitable sheath deployment member including twine; cordage; filament; wire; a line; a band; a strap; a strand; and woven, braided, twisted, knit, looped, linked, metal, plastic, composite materials.

FIGS. 2 and 3 show grooves 58 extending to the shaft distal end 26. Embodiments of the invention may or may not have the grooves 58 extending all the way to the shaft distal end 26 from the shaft proximal end 24.

Figure 5:
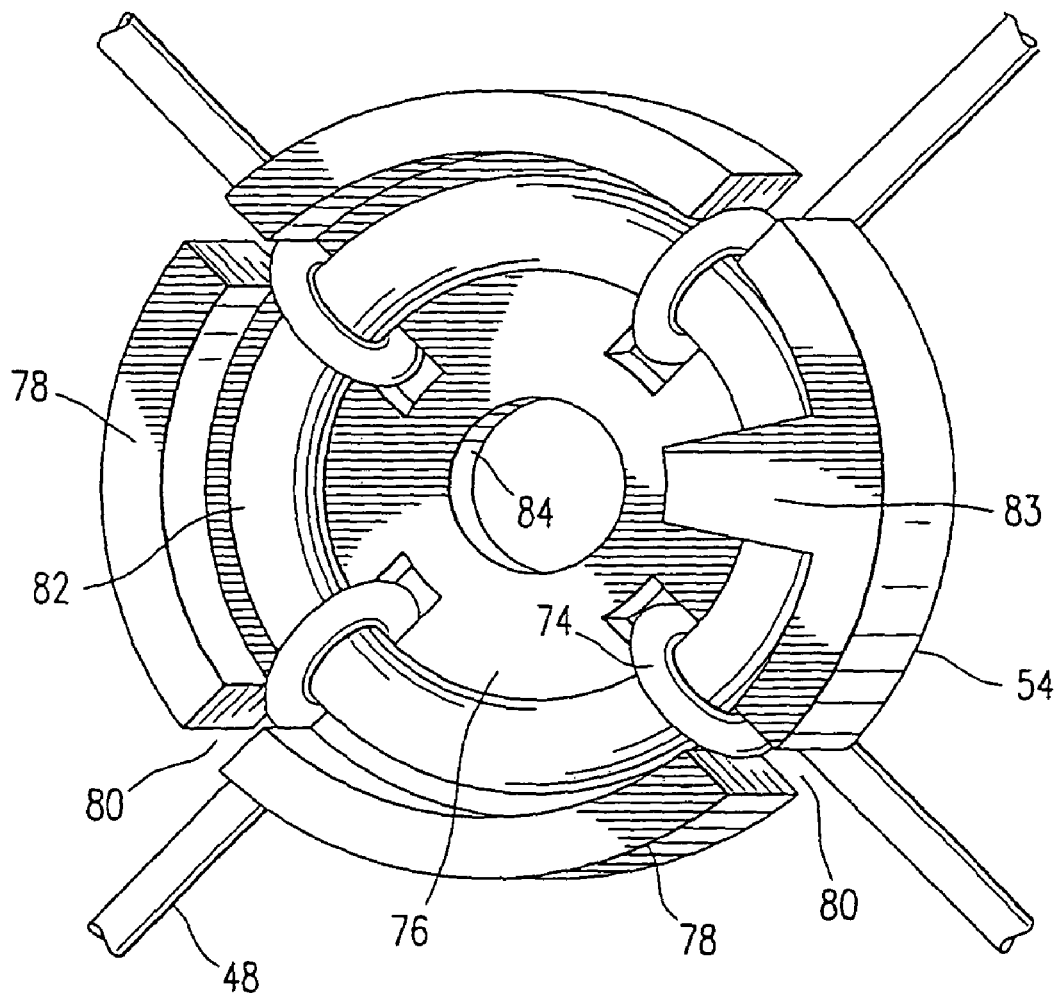
FIG. 5 is a perspective detail view of the inside of a sheath deployment member cap of the device of FIG. 1 with the sheath deployment members looped about a sheath deployment member ring inside the sheath deployment member cap.

Details of how the distal sheath deployment member deployment ends 74 are joined in the end cap 54 are shown in FIG. 5. The end cap 54 comprises a cap top 76 from which extends axial extensions 78 from the periphery in a proximally axial direction. Between each extension 78 is an access slot 80 through which extends the distal sheath deployment member deployment end 74. Each sheath deployment member deployment end 74 is looped around a ring 82 that is disposed inside the end cap 54 and proximate to the cap top 76. The ring 82 is split and has ends (not shown) that abut a radially inwardly extending key 83. The end cap has an axial hole 84 therethrough. The distal end of the sheath deployment member deployment rod 56 (not shown, see FIG. 7) extends through the hole 84 and terminates in a stop 86 disposed on the distal side of the cap top 76 (see FIG. 4).

Referring back to FIG. 4, the device 10 is shown without the outer sleeve 34 to reveal the arrangement of the sheath 14. The sheath 14 comprises the first portion 44 and the second portion 46 with a tissue covering portion therebetween. The first portion 44 is attached to the sheath sleeve 32 distal end 90. In the shown embodiment of the invention, the sheath first portion 44 defines a circular opening in the sheath 14.

The sheath 14 extends distally from the first portion 44 and terminates at the second portion 46. In the shown embodiment of the invention, the sheath 14 is twisted about the shaft 30 much like an umbrella. Other embodiments of the invention may have other arrangements for storing the sheath 14, such as folding the sheath. An opening defined by the second portion 46 is large enough, when fully expanded, to encompass the tissue specimen to be encapsulated. In embodiments of the invention without a sheath sleeve 32 or equivalent, the sheath first portion 44 is attached or otherwise connected to the wand assembly 12.

FIG. 1 shows the sheath second portion 46 extending distally beyond the outer sleeve 34. Other embodiments of the invention may have the outer sleeve 34 covering the sheath second portion 46. Embodiments of the invention may have the outer sleeve 34 proximally slide to facilitate the sheath 14 unfolding during encapsulation of the tissue specimen.

Referring more specifically to FIGS. 4 and 4a, the sheath deployment members 48 are bowed radially outward. The bowing of the sheath deployment members 48 occurs as the respective push rods 52 are distally pushed while the distally located looped deployment end 74 (not shown, see FIG. 5) of each sheath deployment member 48 remains static. The pushing of the rods 52 moves the end balls 70 distally in the grooves 58 and forces the sheath deployment members 48 radially outward. The sheath deployment members 48 extend through ligatures 49 attached to the second portion 46 of the sheath 14. As the sheath deployment members 48 bow outwardly, the sheath deployment members slip through the holes 49 until the end balls 70 comes up against the ligatures 49. The ligature 49 is a looped end of a cord 85 that is embedded in the sheath second portion 46. The ligature 49 is sized such that the end ball 70 cannot slide through it. Other embodiments of the invention may have other equivalent mechanisms and arrangements for attaching the sheath deployment member attachment end 71 to the sheath 14.

Also shown in FIG. 4 is a bowed cutting member 88. The bowed cutting member 88 is shown as being similar to the four sheath deployment members 48. The cutting member 88 is disposed and arranged in the device 10 similar to the sheath deployment members 48. Initially, the cutting member 88 is not fully bowed. Using the fifth push rod 52, the cutting member 88 is forced radially outward through slot 51. In the shown embodiment of the invention, the cutting member 88 is RF powered, as is the member 40 on the tip 38. Other embodiments of the invention may have cutting members that cut through tissue using other means. In some embodiments of the invention, the cutting member may be permanently attached to the distal end of the push rod 52. In other embodiments of the invention, the cutting member 86 may also function similar to the sheath deployment members 48 in drawing the sheath 14 over the tissue specimen as described below. In still other embodiments of the invention, there may not be an element of the device 10 that functions equivalently to the cutting member 88.

Figure 6:
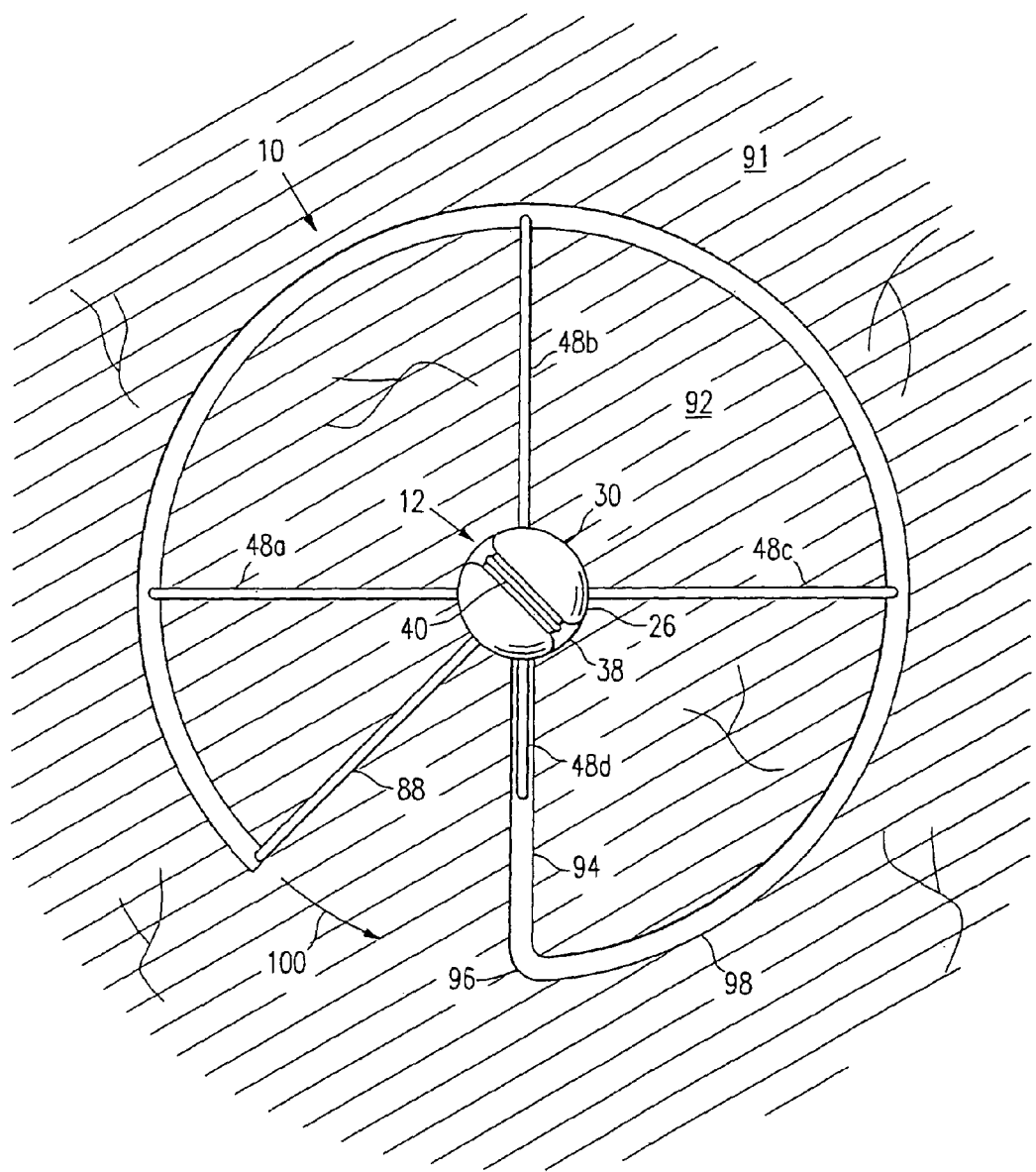
FIG. 6 is a sectional radial view of the device of FIG. 1 in a target body with the sheath deployment members being partially deployed in a periphery margin surrounding the tissue specimen.

Now referring to FIG. 6, the device 10 is shown disposed in a target body 91 with the sheath deployment members 48 partially positioned about a tissue specimen 92. The distal end 26 of the device 10 has been inserted through the tissue specimen 92.

The method for positioning the sheath deployment members 48 about the tissue specimen 92 is that the cutting member 88 is positioned below the shaft 30 and bowed radially outwardly, thereby forming a channel 94 that radially extends from the wand assembly 12. The cutting member 88 is fully bowed and extended when it reaches point 96, which is the beginning of a periphery margin 98. The periphery margin 98 will eventually surround the tissue specimen 92. The device 10 is then rotated in a counter-clockwise direction 100 to start forming the periphery margin 98. Other embodiments of the invention may have the device rotating in a clockwise direction.

After the device 10 has rotated 45 degrees in the counter clock-wise direction 100, the sheath deployment member 48a is aligned with the channel 94. The rotation of the device 10 is halted and the sheath deployment member 48a is radially extended into the channel 94 to point 96. The rotation is re-initiated with the cutting member 88 continuing to create the periphery margin 98 and the sheath deployment member 48a following behind the member in the margin. After the wand 12 has rotated an additional 90 degrees, the rotation is halted and the sheath deployment member 48b is radially extended into the channel 94 to point 96. The rotation of the device 10 is reinitiated with sheath deployment members 48a and 48b following in the margin 98. A similar method is used to deploy sheath deployment member 48c into the margin 98. This may either be done be hand or by directing an actuator system that is functionally attached to the device 10.

FIG. 6 shows the final sheath deployment member, sheath deployment member 48d, partially radially expanded into the channel 94 with 315 degrees of the periphery margin 98 having been formed. The remainder of the method of deploying the sheath deployment members 48 and forming the periphery margin 98 comprises fully extending the sheath deployment member 48d to point 96 and rotating the device 10 until the cutting member 86 reaches point 96, thereby fully forming the periphery margin 98 and separating the tissue specimen 92 from the target body 91. At this point the cutting member 88 may remain bowed or may retracted at least partially back to the shaft 30 by proximally pulling its respective push rod 52 (not shown in FIG. 6).

Figure 7:
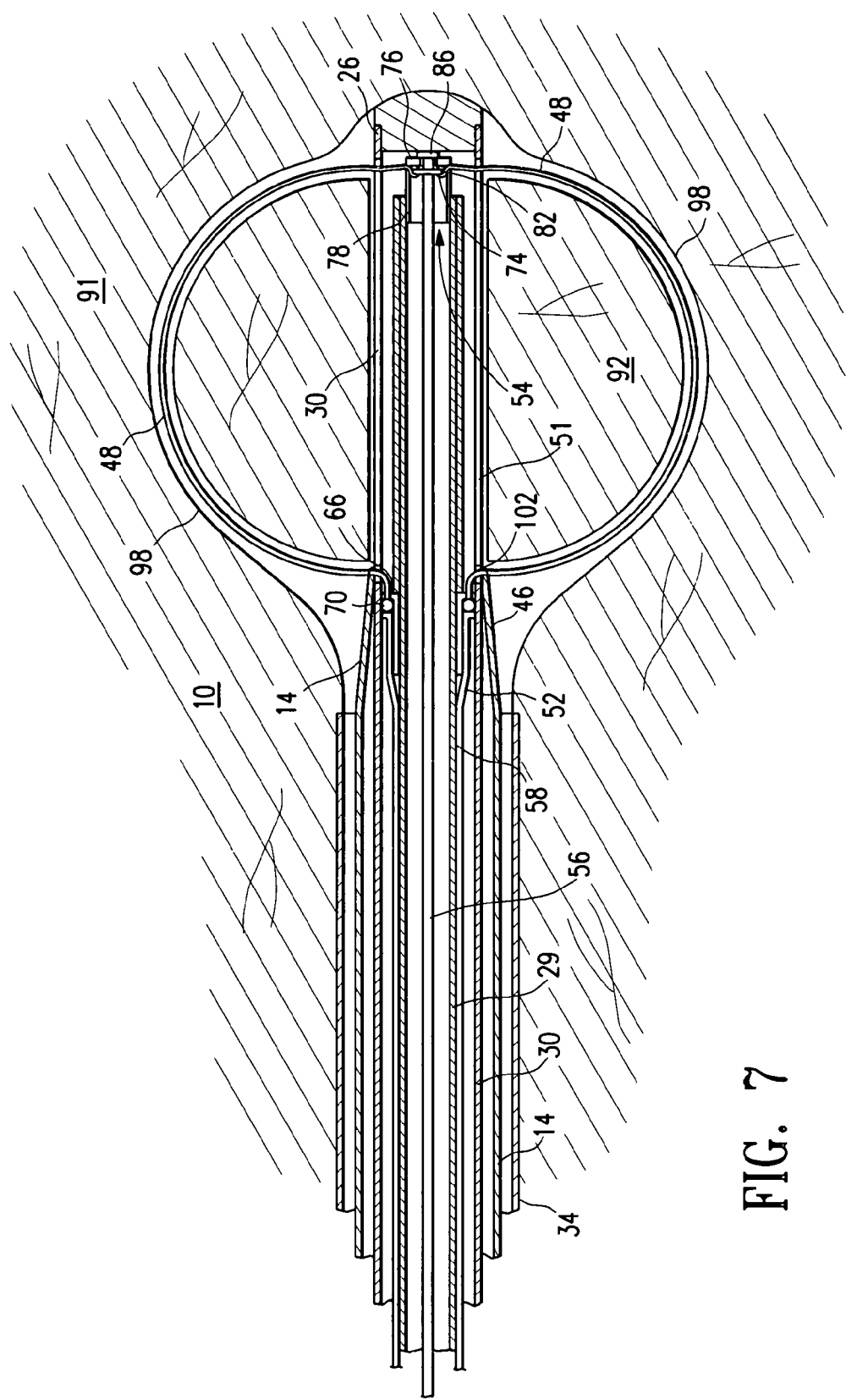
FIGS. 7, 8 and 9 are sectional axial views of the device of FIG. 1 with the tissue specimen in various stages of encapsulation.

Referring now to FIG. 7, the sheath deployment members 48 are shown deployed about the tissue specimen 91. At the axial center of the wand 12 is the sheath deployment member deployment rod 56. The sheath deployment member deployment rod 56 extends, distally through the sheath deployment member cap 54 and terminates at the stop 88. The stop 88 is located distally and adjacent to the cap top 76. The sheath deployment member cap 54 is located at the distal end 26 of the wand assembly 12 with the axial extensions 78 extending proximally. The axial extensions 78 are disposed against the interior surface of the shaft core 29. The sheath deployment member deployment ends 74 are looped around the sheath deployment member ring 82, which is located proximal to the cap top 76. The sheath deployment members 48 extend from the sheath deployment member ring 82 and radially out of the distal end 26 of the shaft 30.

Continuing to refer to FIG. 7, the sheath deployment member deployment rod 56 is centrally located within the shaft core 29. The push rods 52 are disposed in grooves 58 in the outer surface of the shaft core 29. The shaft 30 surrounds the shaft core 29. The tissue specimen 92 is disposed about the shaft 30 toward the shaft's distal end 26. The outer sleeve 34 is shown surrounding the shaft 30 and is located proximally from the tissue specimen 92. The sheath 14 is disposed between the shaft 30 and the outer sleeve 34 with the second portion 46 distally extending from under the outer sleeve.

As depicted in FIG. 7, the sheath deployment members 48 are deployed about the tissue specimen 92 but have not been released from the wand assembly 12. The end balls 70 of the sheath deployment members 48 are disposed in the ball-holders 66. The push rods 52 have been pushed to a position proximal of ball openings 102. The ball openings 102 are located at the proximal end of each sheath deployment member slot 72 and extend through the shaft 30. The ball openings 102 generally correspond with the proximal end of the tissue specimen 92. The sheath deployment members 48 extend from the end balls 70, through the ball openings 102, through ligatures 49 extending from the sheath second portion 46, and into the periphery margin 98 about the tissue specimen 92.

Figure 8:
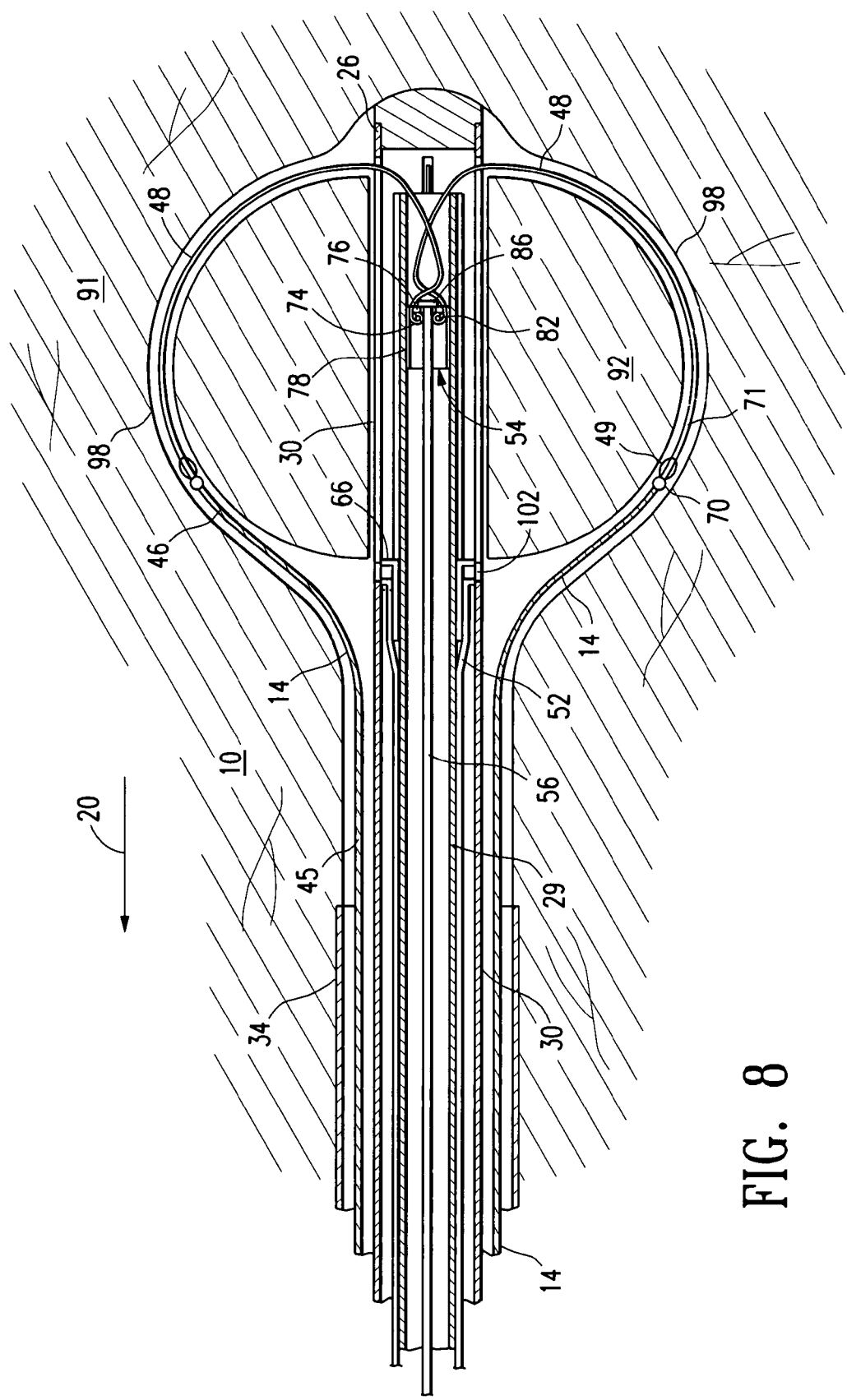

FIG. 8 shows the device 10 after the sheath deployment members 48 have been released and the sheath has been partially drawn into the periphery margin 98. The push rods 52 are positioned to align the ball holders 66 with the ball openings 102. In an embodiment of the invention, the end balls 70 may move out of the ball holders 66 and through the ball opening 102 once the holders and the openings are aligned. In other embodiments of the invention, the ball ends 70 may move when the sheath deployment members 48 have started being pulled through the periphery margin 98 as described below.

To pull the sheath deployment members 48 through the periphery margin 98, the sheath deployment member deployment rod 56 is pulled proximally in the axial direction 20. FIG. 8 shows that the pulled sheath deployment member deployment rod 56 resulted in the sheath deployment member cap 54 being moved axially from the distal end of the device 10. The moving of the sheath deployment member cap 54 resulted in the sheath deployment members 48, which are attached to the sheath deployment member ring 82 in the cap, starting to be drawn into the shaft 30, as is shown in FIG. 8.

As the sheath 14 moves into the periphery margin 98, the sheath starts to encapsulate the tissue specimen 92. Further, in the embodiment shown in the FIGS. 1-8, the sheath sleeve 32 moves distally in the axial direction 20 as it is being drawn by the sheath 14.

Figure 9:
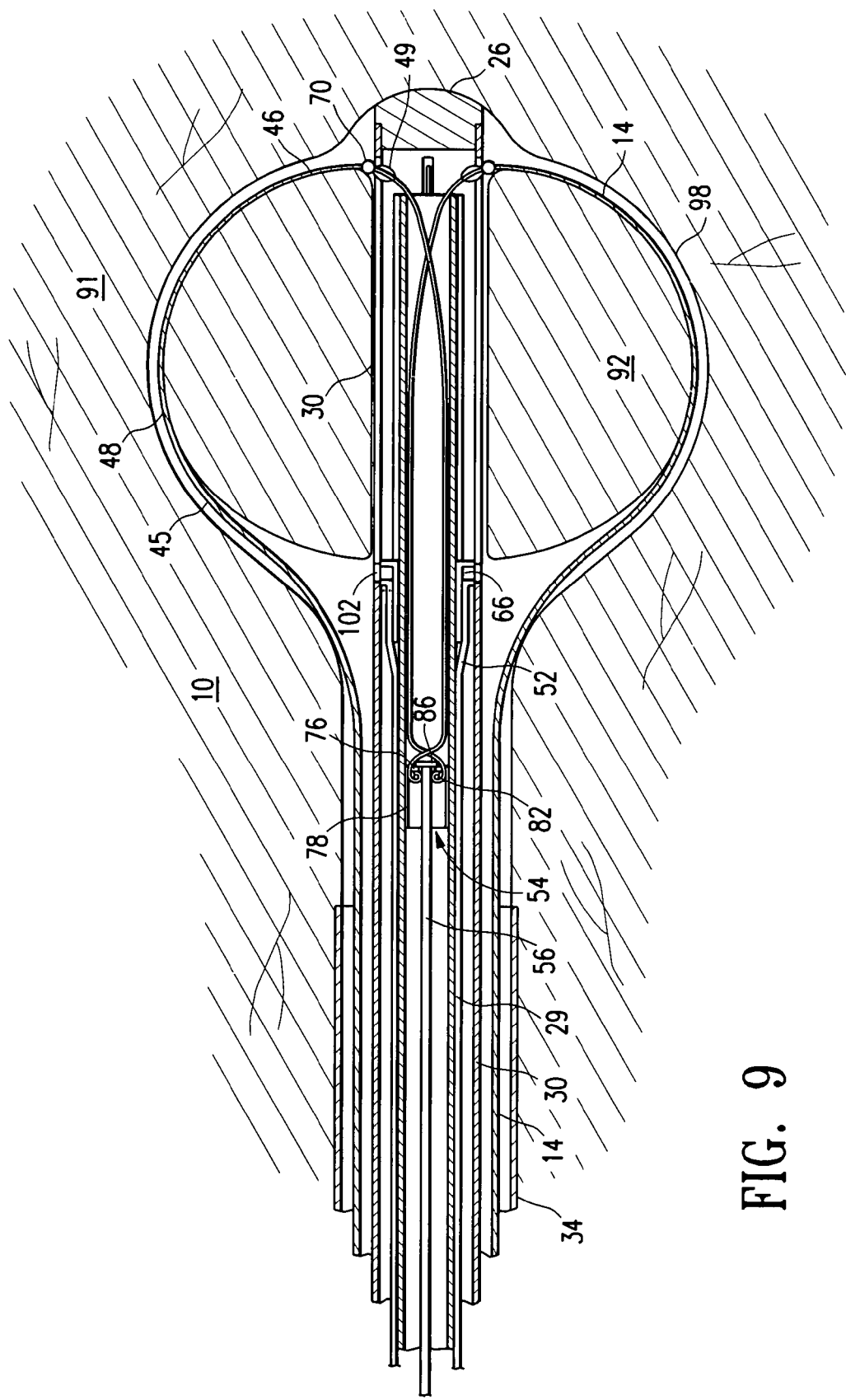

Now referring to FIG. 9, the sheath 14 is shown substantially encapsulating the tissue specimen 92. The end cap 54 has been pulled by the sheath deployment member deployment rod 56 and is in the end cap's proximal most position. The sheath deployment members 48 are disposed in the shaft 30. The end balls 70 of the sheath deployment members 48 are disposed against the shaft 30 at the wand assembly distal end 26. The sheath sleeve 32 (see FIGS. 1 and 5) has been drawn to its distal most position when the tissue specimen 92 has been encapsulated by the sheath 14. Prior to withdrawing the device 10 from the target body, the sheath sleeve 32 may be pulled proximally in the distal direction 20 (see FIG. 1) to tighten the sheath 14 about the tissue specimen 92. The outer sleeve 34 may be pushed distally to tightened the sheath 14 about the tissue specimen 92 also. In an embodiment of the invention, the outer sleeve 34 may be in a more proximal position during the deployment of the sheath 14 to facilitate the sheath emerging from under the outer sleeve during encapsulation.

In an embodiment of the invention, the biopsy tissue specimen encapsulating device 10 is manipulated directly by a user of the device. In another embodiment of the invention, an actuator system (not shown) may be functionally connected to the device 10 to assist in deploying the sheath deployment members 48 and the sheath 14. The actuator system may be secured to the wand assembly 12, the push rods 52, and the deployment rod 56. The actuator system may be able to axially rotate the device 10 and deploy the sheath deployment members 48 as described in connection with FIGS. 6-9. The actuator system may also deploy the sheath 14 by manipulating the deployment rod 56 as described in connection with FIGS. 7-9. Actuators systems in other embodiments of the invention may perform one or more of the operations described herein. Actuator systems may be designed and constructed by those skilled in the art.

In an embodiment of the invention, the device 10 may be arranged such that the RF cutting member 88 remains outwardly radially bowed after the sheath 14 has encapsulated the tissue specimen 92. The cutting member 88 may then be energized as the device 10 with the encapsulated sample 92 is pulled out of the target body 91. The cutting member 88 cuts through the target body 91, thus creating an enlarged passage (not shown) for the tissue specimen 92 to travel through while it is removed from the target body. In other embodiments of the invention, the cutting member 88 is under the sheath 14 and slices through the sheath when energized, thus exposing the cutting member to the target body 91. The cutting member may be aligned with a commissure 111 of the sheath 14 (see FIG. 10*b*). The now exposed cutting member 88 is energized and creates an enlarged passage for the tissue specimen 92 to travel through as it exits the target body 91. In another embodiment of the invention, another cutting mechanism, such as an additional RF cutting member (not shown), is projected radially from the device 10 and proximally from the tissue specimen. The energized, radially projecting cutting member creates an enlarged passage as the device/tissue specimen is pulled from the target body 91. Other embodiments of the invention may have other means for creating an enlarged passage through which the device/tissue specimen may exit the target body 91. Enlarging the exit passage for the tissue specimen 92 to travel through as it exits the target body 91 is to reduce trauma to the body. Embodiments of the invention may use any suitable cutting device to create the enlarged passage, such as the various tools and mechanisms described in connection with the cutting members 40 and 88, and including cryogenic techniques and laser or other focussed light techniques.

Figure 10A:
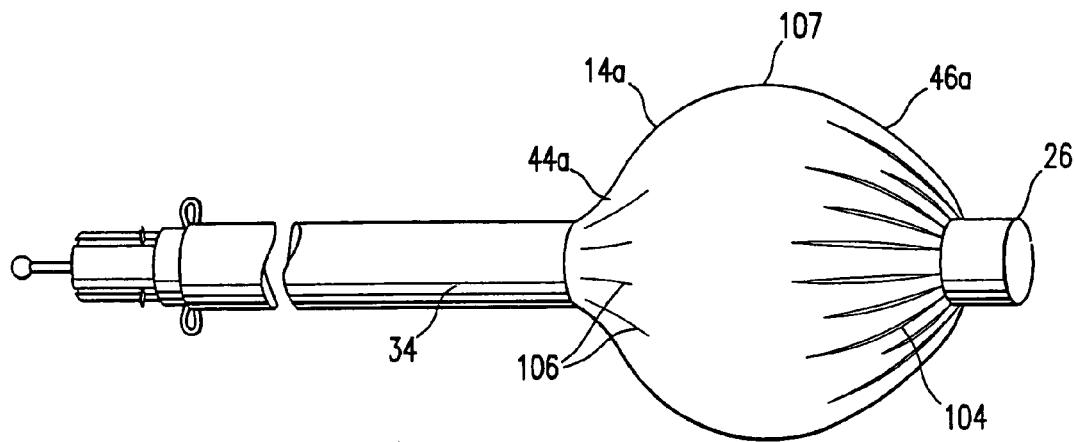
FIGS. 10 a, b, and c are perspective detail views of different sheaths in various stages of encapsulating a tissue specimen for different aspects of the device of FIG. 1.
Figure 10B:
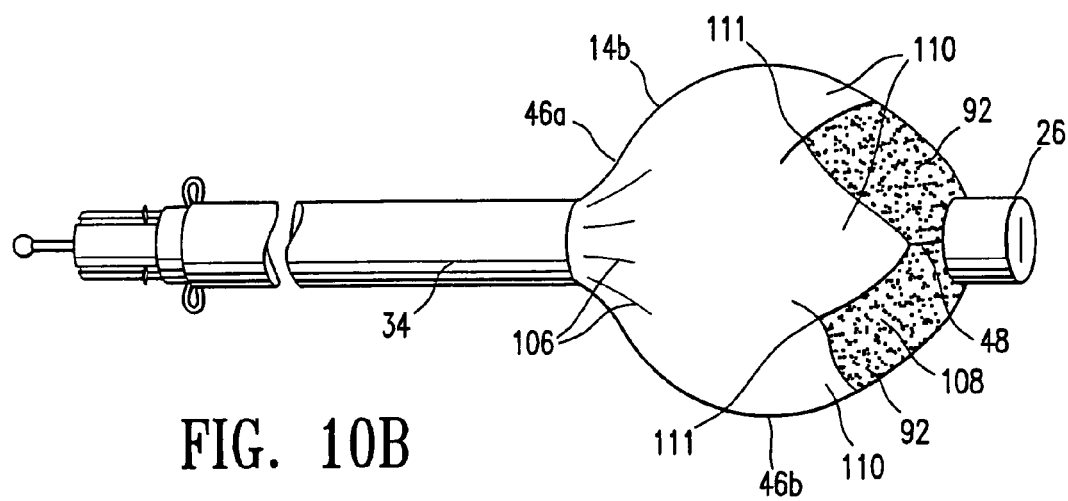
Figure 10C:
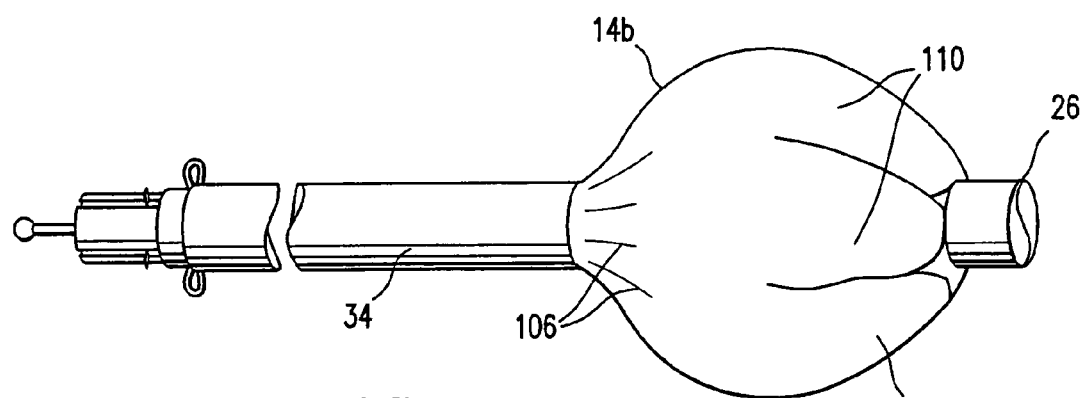

Now referring to FIGS. 10*a* through 10*c*, different embodiments of the invention may have different sheaths. Referring in particular to FIG. 10*a*, the sheath 14*a* substantially encloses the tissue specimen 92. The first portion 44*a* comprises seams 106 such that the first portion fits smoothly over the proximal portion of the tissue specimen 92. The second portion 46*a* has been gathered together into folds 104 at the distal end 28. The second portion 46*a* is gathered into folds as the sheath opening at the second portion 46*a* is round and wide enough to pass over an equator 107 of the tissue specimen 92.

Referring in particular to FIG. 10*b*, the sheath 14*b* is partially drawn over the tissue specimen 92. The second portion 46*b* of the sheath 14*b* does not have a round opening as does sheath 14*a*, but rather has an opening 108 that is formed of peaks 110 and commissures 111. Referring now to FIG. 10*c*, as the tissue specimen 92 becomes substantially encapsulated, the peaks 110 are drawn together and overlap. In another embodiment of the invention, a fully extended sheath may only partially encapsulate the tissue specimen 92, as shown in FIG. 10*b*.

The sheaths 14 of other embodiments of the invention may be of other suitable forms. In an embodiment of the invention, the sheath only partially encapsulates the tissue specimen. In another embodiment of the invention the sheath may comprise multiple pieces such that the sheath is comprised of non-contiguous segments. The sheath may comprise porous material, non-porous material, selectively permeable material, woven material, braided material, knit material, web material, mesh material, film material, flexible laminate material; and/or elastic material.

Now referring to FIGS. 11*a*-11*d*, an embodiment of the invention is shown in which a biopsy tissue specimen encapsulating device 110 has a sheath 112 that is drawn proximally over a tissue specimen 114 as opposed to the sheath 14 that is drawn distally over the tissue specimen 92 in the device 10 previously described. As with the previously described figures, the proximal direction is toward the left of the FIGS. 11*a*-11*d* and the distal direction is toward the right.

The device 110 is comprised of a wand assembly 116, the sheath 112, and a guide assembly 118. The wand assembly 116 comprises an outer sleeve 120 that surrounds a proximal end 122 of a shaft 124. The wand assembly 116 also has a distal end cap 126 at a shaft distal end 128. In the shown embodiment of the invention, the distal end cap 126 does not have an RF member that may be energized such that the device 110 moves through tissue, thus enabling the device to be inserted into the target containing a tissue specimen to be encapsulated. Other embodiments of the invention may have an RF powered member on the distal end cap 126 or some other means of enabling the device 110 to be inserted into the target, as was previously described in connection with device 10.

Figure 12A:
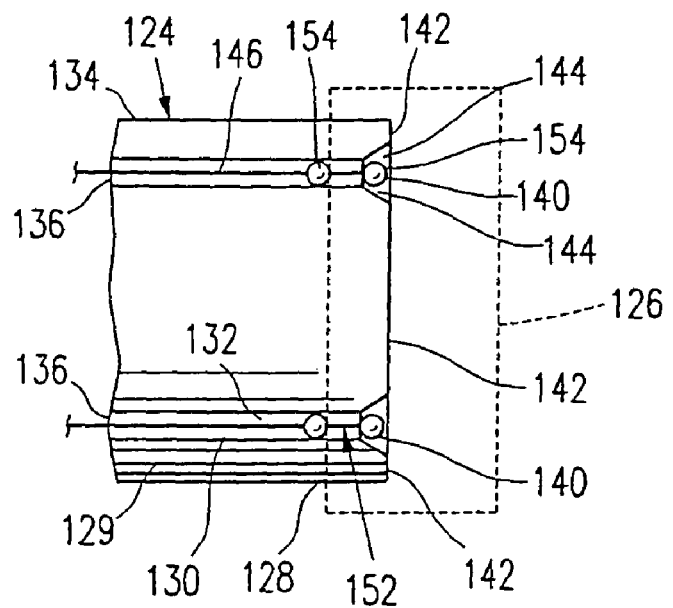
FIGS. 12a-b are details of the device of FIGS. 11a-d.
Figure 12B:
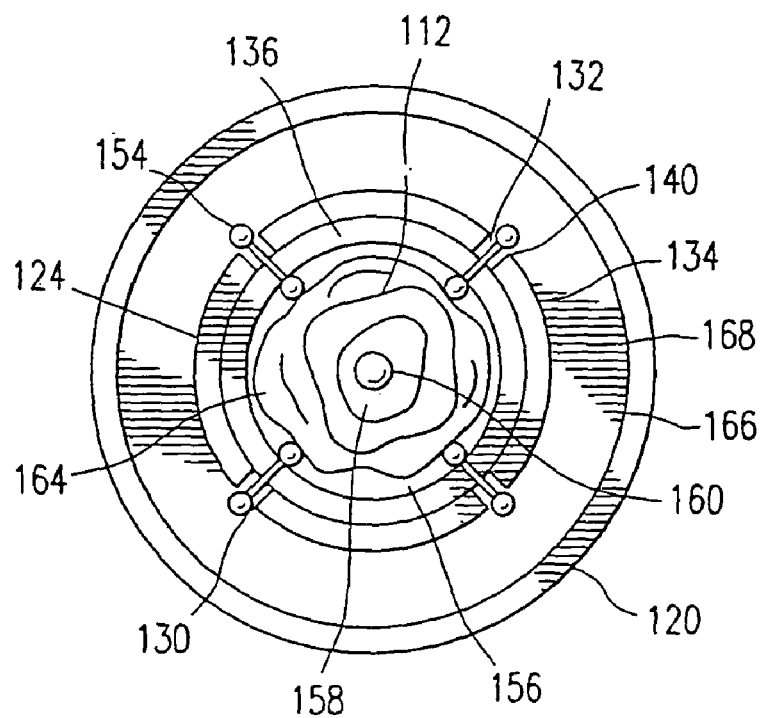

The shaft 124 of the wand assembly 116 has an outside surface 129 with axially directed grooves 130 extending along it. Details of the grooves 130 are shown in FIGS. 12*a* and 12*b*. The grooves 130 are defined by gaps 132 in an outer portion 134 of the shaft 124. The shaft outer portion 134 is of a cylindrical shape and is mounted to and about a shaft inner portion 136. The shaft inner portion 136 is a cylinder. The axially aligned gaps 132 in the shaft outer portion 134 and the shaft inner portion 136 define the grooves 130.

The grooves 130 of the shaft 124 terminate at a shaft distal end 128 at notches 140. The notches 140 are formed by the distal end 142 of the outer shaft portion 134 extending beyond the shaft inner portion 136. The notches 140 are shown with beveled edges 144. Other embodiments of the invention may have notches of other arrangements and configurations.

Sheath deployment members 146 of the guide assembly 118 are initially disposed in the grooves 130, as is shown in FIGS. 11a, 12a and 12b. The sheath deployment members 146 have a proximal end 148 with an extending member 150 for pushing the sheath deployment members distally and pulling the sheath deployment members axially. The sheath deployment members 146 also have a distal end 152 with a double ball ending 154 that straddles a respective notch 140, as is shown in FIG. 12b, thereby anchoring the sheath deployment member distal ends in the notches. The distal end cap 126 of the wand assembly 116 is shown in FIGS. 11a and 12a disposed against the shaft distal end 128. By being disposed against the distal end 128, the distal end cap 126 prevents the double ball endings 154 of the sheath deployment members 146 from moving out of the straddling position shown in FIG. 12b.

Referring now to FIG. 12b, the sheath 112 of the device 110 is stored in an interior 156 of the shaft 124 prior to use of the device. The shaft interior 156 is defined by the shaft inner portion 136. The sheath 112 has a first portion 158 that is slidably connected to a distal end cap rod 160 such that the rod extends through the sheath. The distal cap end rod 160 extends proximally from the distal end cap 126, through shaft interior 156, and terminates at a proximal end 162 that extends beyond the shaft proximal end 122. Other embodiments of the invention may use other means for connecting the sheath first portion 158 to the distal end cap rod. Further, other embodiments of the invention may have the sheath first portion 158 attached to the shaft 124 or the distal end cap 126. The sheath 112 is folded into the shaft interior 156 as is shown in FIG. 12b. Other embodiments of the invention may have the sheath stored in the shaft interior 156 in other suitable arrangements. The sheath deployment member double-ball endings 154 are attached to a sheath second portion 164.

Other embodiments of the invention may have other arrangements for storage of the sheath 112 and securing the sheath deployment member distal ends 152. In an embodiment of the invention, the sheath second portion 164 extends radially beyond the shaft distal end 128 such that the second portion is secured in place when the distal end cap 126 is seated against the shaft distal end. In this embodiment, the sheath deployment member distal ends 152 are temporarily secured in place while the distal end cap remains seated.

Referring specifically to FIG. 12b, the shaft 124 is axially centered within the outer sleeve 120 by a bushing 166 that is in an annular gap 168 between the shaft and outer sleeve. Other embodiments of the invention may have other means for securing and/or centering the shaft 124 within the outer sleeve 120.

Referring specifically to FIG. 11a, the device 110 is shown prior to deployment of sheath deployment members 146. The shown embodiment comprises four sheath deployment members 146, with two sheath deployment members being shown. The sheath deployment members 146 are in the grooves 130 (as shown in FIG. 12a) on the shaft outside surface 129 in a similar fashion to the sheath deployment members 48 in grooves 58 of the device 10. The sheath deployment members 146 extend proximally under the outer sleeve 120 with the sheath deployment member proximal ends 148 extending past the sleeve proximal end 169. The sheath deployment member proximal ends 148 are shown in a first position 172. The sheath deployment member distal ends 152 are secured by the distal end cap 126 as previously described. In other embodiments of the invention, each sheath deployment member 146 may be made of one or more pieces.

FIG. 11a also shows the distal end cap rod 160 is also shown in its first, or initial position 174. The distal end cap rod 160 extends proximally from the distal end cap 126, through the center of the shaft 124, and terminates beyond the shaft distal end 128. With the distal end cap rod 160 in the first position 174, the distal end cap 126 is temporarily seated on the shaft distal end 128 and the sheath deployment member distal ends 152 secured in place, as was previously described.

Now referring specifically to FIG. 11b, the sheath deployment members 146 have been deployed to a radially bowed position. To radially extend the sheath deployment members 146, the proximal sheath deployment member ends 148 are distally pushed to a sheath deployment member end second position 176, as is shown. The distal end cap 126 is still seated on the shaft distal end 128 and secures the sheath deployment member distal ends 152. Therefore, the distal end cap rod 160 remains in the first position 174. The device 110 is shown without a tissue specimen in FIG. 11b to more clearly show the deployment of the sheath deployment members 146. During use of the device 110, the sheath deployment members 146 would be deployed about a tissue specimen in much the same manner as is described in connection with FIG. 7 either with or without a cutting member incorporated into the device 110.

Now referring specifically to FIG. 11c, the sheath 112 has been partially deployed about the tissue specimen 114. To release the sheath 112 from the shaft interior 156, the distal end cap rod 160 is pushed distally to a second position 180, thus unseating the distal end cap 126. With the distal end cap 126 unseated, the double ball endings 154 of the sheath deployment member distal ends 152 are no longer secured in the notches 140. As the sheath deployment members 146 are pulled proximally, the double-ball endings 154 slide through the notches 140. As the second portion 164 of the sheath 112 is attached to the double ball endings 154, the sheath 112 slides out of the shaft interior 156 and over the tissue specimen 114. The proximally pulled sheath deployment members 146 are shown in a third position 182, which places the sheath deployment member proximal ends 148 in a more proximal location compared to the first position 172 and the second position 176 shown respectively in FIGS. 11a and 11b.

Now referring specifically to FIG. 11d, the sheath 112 has been fully deployed about the tissue specimen 114. The sheath deployment member proximal ends 148 are shown pulled to a final position 184, which is the most proximal of all the sheath deployment member positions. The distal end cap 126 is shown reseated on the shaft distal end 128, with the distal end cap rod 160 being in its proximally located final position 186. The seating of the distal end cap 126 secures the sheath 112 to the shaft distal end 128, which assists in preventing the tissue specimen 114 from sliding distally relative to the shaft 124 as the specimen is removed from a target body. Other embodiments of the invention may have other means for preventing the relative distal sliding of the tissue specimen 178, or not have such a means. The sheath second portion 164 is under the outer sleeve 120 to prevent the sheath 112 from snagging on the target body during removal of the assembly 110. Other embodiments of the invention may have the outer sleeve 120 be able to slide axially such that the sheath 112 may be pushed up against the tissue specimen 178 thereby snugly securing the sheath against the specimen.

Referring to FIGS. 13, 14a, and 14b, a biopsy tissue specimen encapsulating device 200 is comprised of a guide assembly 202 that is capable of moving rotationally a sheath 204 about a tissue specimen 205. The device 200 comprises the guide assembly 202, the sheath 204, and a wand assembly 206, which are analogous to the components of the previously described devices 10 and 110.

More specifically, in the shown embodiment of the invention, the guide assembly 202 is capable of moving rotationally a sheath second portion 208 about an axis of rotation that is parallel to an axis 210 of the wand assembly 206. The guide assembly 202 is comprised of a wrapper assembly 212 that is shown in a radially bowed position in FIG. 13. Prior to insertion of the device 200 into a target body 214, the wrapper assembly 212 lies against a shaft 216 of the wand assembly 210.

After insertion of the device 200 into the target body 214, the wrapper assembly 212 is bowed radially outward. In some embodiments of the invention, the wrapper assembly 212 is bowed radially outward by a push rod (not shown) that is distally pushed. FIG. 14a shows the wrapper assembly 212 after it has been bowed and has passed through a radial margin 218 in the tissue specimen 205.

The wrapper assembly comprises a housing 220 in which the sheath second portion 208 is furled. The first portion 222 of the sheath 214 is connected to the wand assembly 206. As the housing 220 is rotated through a periphery margin 224 about the tissue specimen 205, the sheath second portion 208 unfurls from the housing 220 and encapsulates the specimen, as is shown in FIG. 14b.

Referring now to FIGS. 15, 16a and 16b, a biopsy tissue specimen encapsulating device 230 is comprised of a guide assembly 232 that is capable of moving rotationally a sheath 234 about the tissue specimen 205. The device 230 comprises the guide assembly 232, the sheath 234, and a wand assembly 236, which are analogous to the components of the previously described device 200.

More specifically, in the shown embodiment of the invention, the guide assembly 232 is capable of moving rotationally a sheath second portion 238 about an axis of rotation that is parallel to an axis 240 of the wand assembly 236. The guide assembly 232 is comprised of an arm 242 that is shown in a radially bowed position in FIG. 15. Prior to insertion of the device 230 into the target body 214, the arm 242 lies against a shaft 246 of the wand assembly 236.

After insertion of the device 230 into the target body 214, the arm 242 is bowed radially outward. In some embodiments of the invention, the arm 242 is bowed radially outward by a push rod (not shown) that is distally pushed. FIG. 16a shows the arm 242 after it has been bowed and has passed through a radial margin 218 in the tissue specimen 205.

The wrapper assembly comprises the arm 242 to which the sheath second portion 238 is attached. The first portion 252 of the sheath 234 is connected to the shaft 246 with the sheath 214 being stored in the shaft. As the arm 242 is rotated through a periphery margin 224 about the tissue specimen 205, the arm 242 pulls the sheath 214 from the shaft 246 and over the tissue specimen 205, thus encapsulating the specimen, as is shown in FIG. 16b.

Figure 17:
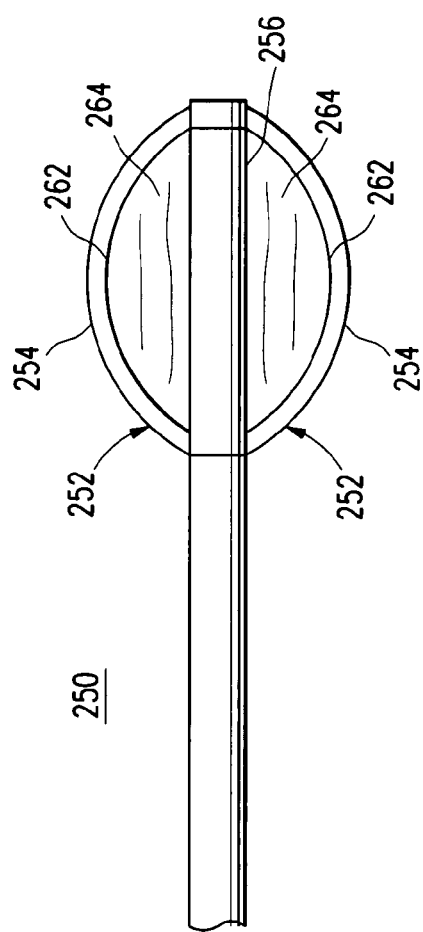
FIG. 17 is a side view of a biopsy tissue specimen encapsulating device that rotationally encapsulates a tissue specimen with two rotating arms according to an embodiment of the invention.
Figure 18B:
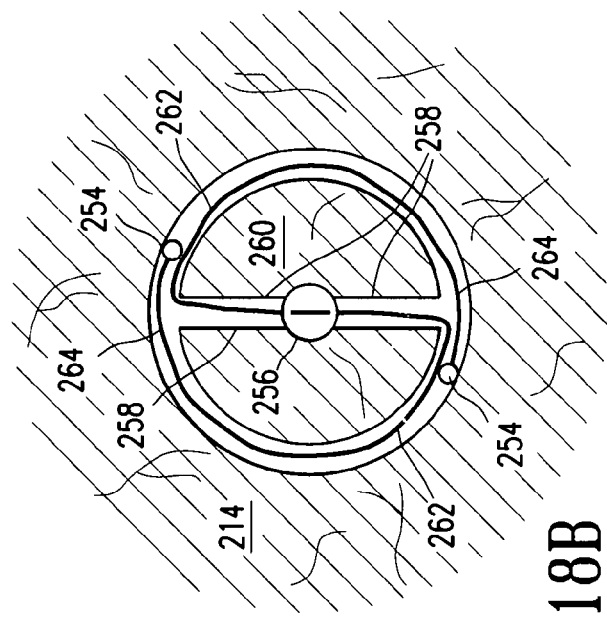
FIGS. 18a-b are sectional views of the device of FIG. 17 at various stages of encapsulation of the tissue specimen.
Figure 18A:
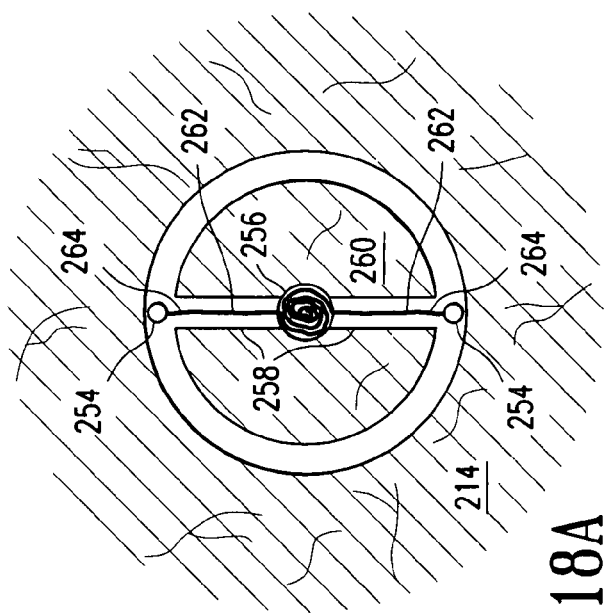

Now referring to FIGS. 17, 18a and 18b, a biopsy tissue specimen encapsulating device 250 comprises a dual rotational guide assembly 252, similar to the guide assembly 232 of device 230 but with two arms 254. Prior to use, the arms 254 are disposed in or on a shaft 256 with the sheath 262 being stored in the shaft. The arms 254 are radially bowed away from the shaft 256 through opposing radial margins 258 in the tissue specimen 260, bringing with them second portions 264 of the sheath 262, as is shown in FIG. 18a.

To encapsulate the tissue specimen 260, the arms 254 are rotated about the specimen in an approximately 180 degree arc, instead of the approximately 360 arc of the device 230, pulling the second portions 264 over the specimen and encapsulating it, as is shown in FIG. 18b. In the shown embodiment of the invention, the sheath 260 may be in two parts, with the sheath first portions (not shown) attached to each other or attached to the shaft 256. Additionally, in the shown embodiment of the invention, the sheath 260 may be of one piece with two opposing second portions 264 attached to the arms and essential not have a definite demarcation for respective first portions.

In another embodiment of the invention, a guide assembly may have two opposing wrapper assemblies as is shown in FIGS. 13, 14a and 14b. Other embodiments of the invention may have more that two arms or wrapper assemblies, or a combination of arm(s) and wrapper assembly(ies). Other embodiments of the invention may also have a cutting means, such as an RF member, preceding the guide assembly and forming the radial and periphery margins.

Figure 19:
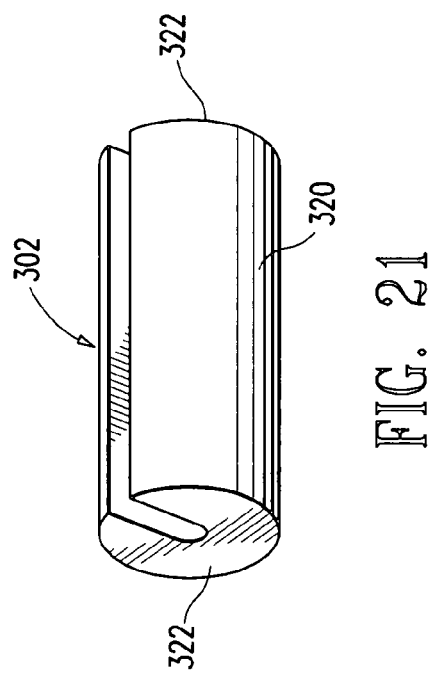
FIG. 19 is a sectional radial view of a biopsy tissue specimen encapsulating device that encapsulates a tissue specimen adjacent to the shaft of the device according to an embodiment of the invention.

Referring now to FIG. 19, in the shown embodiment of the invention, a biopsy tissue specimen encapsulating device 270 comprises a shaft 272 that is placed adjacent to a tissue specimen 274, rather than through a tissue specimen as is previously described. Device 270 incorporates the use of a guide assembly 276 that is similar to the guide assembly 232 of device 230. The guide assembly 276 comprises an arm 278 to which is attached a second portion 280 of a sheath 282. The first portion 284 of the sheath 282 is stored in a shaft 272. As the arm 278 is rotated about a periphery margin 288 surrounding the tissue specimen 274, the sheath 282 is pulled over the specimen and encapsulates it. This embodiment of the invention may also incorporate the wrapper assembly 212 as shown in FIG. 13 instead of the arm 278. This embodiment may be useful in removing small tissue specimens instead of a device that pierces the specimen. This embodiment may also be useful for encapsulating tissue specimens proximate to a boundary that is undesirable to disturb with a rotating cutting member or other periphery forming device, such as a tumor near the skin or an organ.

Figure 21:
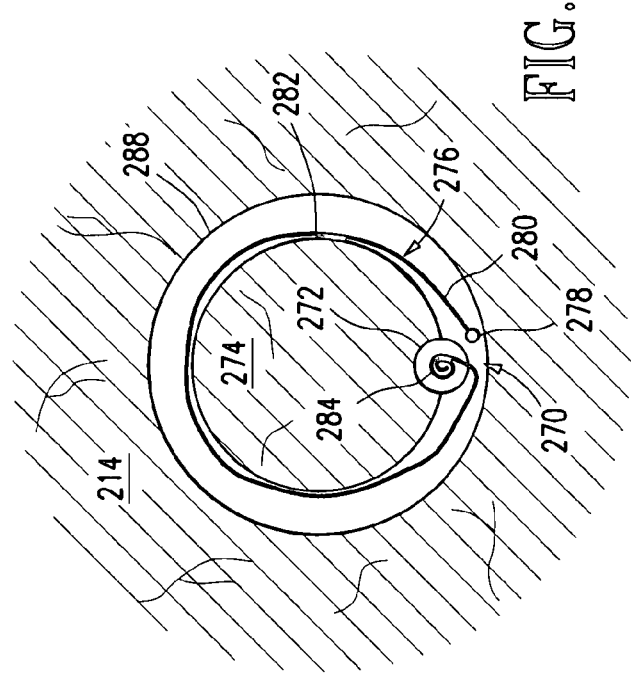
FIG. 21 is a perspective view of the cylindrically shaped tissue specimen that is encapsulated by the device of FIG. 20.
Figure 20:
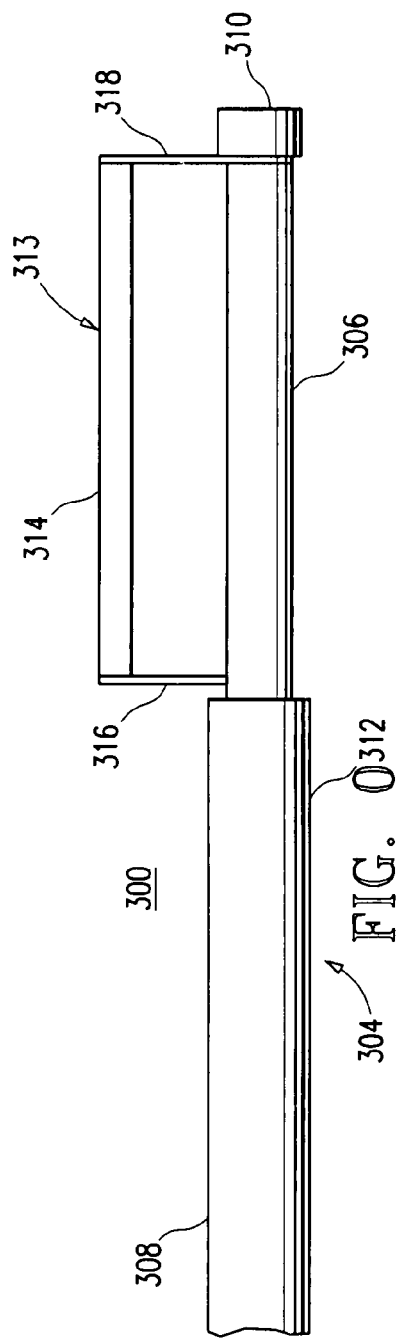
FIG. 20 is a biopsy tissue specimen encapsulating device for rotationally encapsulating a cylindrically shaped tissue specimen according to an embodiment of the invention.

Referring now to FIGS. 20 and 21, a biopsy tissue specimen encapsulating device 300 is designed to encapsulate a cylindrically shaped tissue specimen 302. The device 300 comprises a wand assembly 304 with a shaft 306 having a proximal end 308, shown to the left, a distal end 310, shown to right, and a midportion 312 therebetween. The device 300 also has a guide assembly 313 comprising a straight wrapper assembly 314 with a first end 316 that is proximally located and a second end 318 that is distally located. The first end 316 connects to the shaft midportion 312 and the second end 318 connects to the shaft distal end 310. The ends 316 and 318 are shown as radially extending members.

To encapsulate the cylindrically shaped tissue specimen 302, the wrapper assembly 314 is rotated about a curved surface 320 of the specimen as the sheath (not shown) unfurls from the assembly 314. In the shown embodiment of the invention, the flat, circular ends 322 of the specimen 302 would not be covered with a sheath (not shown) unfurling from the wrapper assembly 314, therefore the specimen is partially encapsulated. Other embodiments of the invention may have ends 316 and 318 that dispose end sheaths (not shown), over the specimen cylindrical ends 322. The end sheaths and the sheath covering the curved surface 320 may or may not be unitary.

Referring to FIGS. 22 and 23, a biopsy tissue specimen encapsulating device 330 is designed to encapsulate a truncated cone shaped tissue specimen 332. The device 330 comprises a wand assembly 334 with a shaft 336 having a proximal end 338, shown to the left, a distal end 340, shown to right, and a midportion 342 therebetween. The device 330 also has a guide assembly 344 comprising a straight wrapper assembly 346 with a first end 348 that is proximally located and a second end 350 that is distally located. The first end 348 connects to the shaft midportion 342 and the second end 350 connects to the shaft distal end 340. The ends 348 and 350 are shown as radially extending members.

In the shown embodiment of the invention, the ends 348 and 350 are of different lengths. More specifically, the first end 348 that connected to the shaft midportion 342 is shorter than the second end 350 that is connected to the shaft distal end 340. With this arrangement, the ends 348 and 350 and the wrapper assembly 345 complement a proximate circular end 352, a distal curved end 354, and a curved surface 356 of the tissue specimen 332, respectively, during the rotation of the guide assembly 344 during the encapsulation of the specimen. The encapsulation of the truncated cone shaped tissue specimen 332 occurs in a manner similar to the encapsulation of the cylindrically shaped tissue specimen 302 with the device 300.

Referring to FIGS. 24 and 25, a biopsy tissue specimen encapsulating device 360 is designed to encapsulate a multi-surface tissue specimen 362. The multi-surface specimen 362 is still of a rotational form, as is the cylindrically shaped tissue specimen 302 and the truncated cone shaped tissue specimen 332. However, whereas there is only a single curved surface in specimens 302 and 332, the multi-surface specimen 362 has a proximate curved surface 364 and a distal curved surface 366.

The device 360 for encapsulating the multi-surface tissue specimen 262 comprises a wand assembly 368 with a shaft 370 having a proximal end 372, shown to the left, a distal end 374, shown to right, and a midportion 376 therebetween. The device 360 also has a guide assembly 378 comprising a bent wrapper assembly 380. The bent wrapper assembly 380 complements the proximate and distal curved surfaces 364 and 366 of the multi-surface tissue specimen 262. The guide assembly further comprises a first end 382 that is proximally located and a second end 384 that is distally located. The first end 382 connects to the shaft midportion 376 and the second end 384 connects to the shaft distal end 374. The ends 382 and 384 are shown as radially extending members. The encapsulation of the multi-surface tissue specimen 332 occurs in a manner similar to the encapsulation of the cylindrically shaped tissue specimen 302 with the device 300 and the truncated cone shaped tissue specimen 362 with the device 330.

In other embodiments of the invention, the wrapper assembly may be of any suitable form to complement the curved surface or surfaces of a specific tissue specimen. Further, the wrapper assembly may be at least partially curved in some embodiments of the invention. In the shown embodiments of the invention, the first and second ends of the wrapper assembly are parallel. In other embodiments of the invention, the ends may not be parallel. In the shown embodiments of the invention, the first and second ends of the wrapper assembly are straight. In other embodiments of the invention, the ends may be of any shape and may comprise more than one element, mother embodiments of the invention, there may be only one end comprising an extending member. In some embodiments of the invention, cutting means, such as an RF member, may be incorporated to lead the guide assembly during the encapsulation to form the periphery margin about a tissue specimen, as was previously described.

Other embodiments of the invention may at least partially encapsulate a number of different tissue specimen shapes. Referring now to FIGS. 26a-g, a non-exclusive set of examples of different tissue specimen shapes are shown.

Embodiments of the invention may encapsulate tissue specimens of partial rotations or full rotations that have been segmented or otherwise sectioned. In FIG. 26a, an axially-halved cylindrically shaped tissue specimen 400 has a curved surface 402 that extends between a circular perimeter 404 of two half circular ends 406 and between the longitudinal edges 408 of a rectangular surface (not shown) that extends through the specimen's major axis 410. The tissue specimen 400 may be the result of full cylindrical tissue specimen that was axially split or the result of a partial rotation. In an embodiment of the invention, the encapsulating device (not shown) may deploy the guide assembly radially, accomplish a 180 degree rotation, and retract the guide assembly to the shaft of the device.

In FIG. 26b, a tissue specimen 412 having the shape of a segment of a cylinder has a partial curved cylindrical surface 414 extending between a circular perimeter 416 of two circular segment ends 418 and between the longitudinal edges 420 of two rectangular surfaces 422 that form an angle 424 at the major axis 426 of the full cylindrical form (not shown). While the tissue specimen 412 depicts the angle 424 having less than 180 degrees, embodiments of the invention may also encapsulate specimens with an angle of greater than 180 degrees. The tissue specimen 412 may be encapsulated in a manner similar to that described in connection with the axially-halved cylindrically shaped tissue specimen 400.

In FIG. 26c, a tissue specimen 428 having the shape of a segment of a sphere has a partial curved spherical surface 430 bounded by a circular perimeter edge 432 of two half circular sides 434 that form an angle 436 at the axis 438 of the full spherical shape (not shown). The angle 436 may be less than or greater than 180 degrees.

In embodiments of the invention, the encapsulation of tissue specimens of partial rotations may be practiced for a number reasons. One such reason is that the partial rotation tissue specimen is more desirable to remove from the target body than a whole rotation tissue specimen from a stand point of reducing trauma to the target body. Another reason is that the shape and/or location of a lesion in the tissue specimen lends itself to be surrounded by partial rotation.

Referring now to FIGS. 26d-g, embodiments of the invention may encapsulate an eccentric rotation tissue specimen 440, an irregular surface rotational tissue specimen 442, an oblate ellipsoid tissue specimen 444, and a prolate ellipsoid tissue specimen 446. Other embodiments of the invention may encapsulate tissue specimens of combinations of those disclosed or tissue specimens of other shapes.

While the encapsulation of a partial and full rotation tissue specimens has been disclosed in the context of rotationally surrounding the specimen with a sheath, other embodiments of the invention may encapsulate these specimens by axially drawing the sheath over it.

Although presently preferred embodiments of the present invention have been described in detail hereinabove, it should be clearly understood that many variations and/or modifications of the basic inventive concepts herein taught, which may appear to those skilled in the pertinent art, will still fall within the spirit and scope of the present invention, as defined in the appended claims.

What is claimed is:

1. A device for encapsulating a tissue specimen prior to withdrawal from a body, the device comprising:
   a. a wand assembly defining an axis, an axial direction, and a radial direction;
   b. a sheath at least partially contained within the wand assembly, the sheath comprising a first proximal portion being connected to the wand assembly and a second distal portion; and
   c. a guide assembly connected to the second distal portion, the guide assembly being configured such that proximal movement of the guide assembly distally extends the sheath from within the wand assembly to position the sheath about at least a portion of the tissue specimen to at least partially encapsulate the tissue specimen.

2. The encapsulating device of claim 1, wherein the sheath comprises a plurality of non-contiguous segments.

3. The encapsulating device of claim 2, wherein adjacent non-contiguous segments overlap when the sheath is positioned about at least a portion of the tissue specimen.

4. The encapsulating device of claim 1, wherein the guide assembly is configured to move the sheath second portion in the axial direction.

5. The encapsulating device of claim 1, wherein the guide assembly is configured to move the sheath second portion in a direction that is not the axial direction.

6. A device for encapsulating a tissue specimen prior to withdrawal from a body, the device comprising:
   a wand assembly defining an axis, an axial direction, and a radial direction;
   a sheath comprising a first proximal portion being connected to the wand assembly and a second distal portion; and
   a guide assembly connected to the second distal portion, wherein proximal movement of the guide assembly positions the sheath about at least a portion of the tissue specimen to at least partially encapsulate the tissue specimen, wherein:
   the sheath first portion is attached to the wand assembly;
   the sheath extends from the first portion and terminates at the second portion; and the sheath second portion defines an opening in the sheath through which a distal portion of the wand assembly extends, wherein the opening has a diameter of at least a maximum cross-section of the tissue specimen in a plane that is generally normal to the wand assembly axis.

7. The encapsulating device of claim 6, wherein the guide assembly comprises at least a sheath deployment member having an attachment end and a deployment end, the attachment end being attached to the sheath second portion, the sheath deployment member being arranged such that moving the sheath deployment member deployment end in the wand assembly axial direction results in the sheath deployment member guiding the second portion opening over the tissue specimen.

8. A device for encapsulating a tissue specimen prior to withdrawal from a body, the device comprising:
   a wand assembly defining an axis, an axial direction, and a radial direction; a flexible sheath configured for deployment around the tissue specimen, the flexible sheath including a first proximal portion connected to the wand assembly and a second distal portion; and
   a guide assembly including at least a sheath deployment member having an attachment end and a deployment end, the attachment end being attached to the flexible sheath second distal portion, the sheath deployment member being configured such that proximal movement of the sheath deployment member deployment end in the wand assembly axial direction results in the sheath deployment member attachment end guiding the flexible sheath second distal portion over the tissue specimen,
   wherein the second distal portion of the flexible sheath has an end opening, and the guide assembly being configured to expand the end opening and then contract the end opening during the proximal movement of the sheath deployment member deployment end in the wand assembly axial direction as the flexible sheath second distal portion is guided over the tissue specimen.

9. The device of claim 8, wherein proximal movement of the sheath deployment member deployment end in the wand assembly axial direction results in distal movement of the flexible sheath to advance the flexible sheath second distal portion in a distal axial direction over the tissue specimen.

* * * * *